US010874721B2

(12) United States Patent
Li

(10) Patent No.: US 10,874,721 B2
(45) Date of Patent: Dec. 29, 2020

(54) METHOD FOR PREVENTING AND TREATING CERVICAL EROSION

(71) Applicant: Talengen International Limited, Discovery Bay (HK)

(72) Inventor: Jinan Li, Shenzhen (CN)

(73) Assignee: Talengen International Limited, Wanchai (HK)

(*) Notice: Subject to any disclaimer, the term of this patent is extended or adjusted under 35 U.S.C. 154(b) by 45 days.

(21) Appl. No.: 16/062,410

(22) PCT Filed: Dec. 16, 2016

(86) PCT No.: PCT/CN2016/110454
§ 371 (c)(1),
(2) Date: Jun. 14, 2018

(87) PCT Pub. No.: WO2017/101872
PCT Pub. Date: Jun. 22, 2017

(65) Prior Publication Data
US 2019/0151422 A1    May 23, 2019

(30) Foreign Application Priority Data

Dec. 18, 2015 (WO) ................ PCT/CN2015/097948

(51) Int. Cl.
*A61K 38/48* (2006.01)
*A61K 38/00* (2006.01)
*A61P 15/02* (2006.01)
*A61K 9/00* (2006.01)
*A61K 45/06* (2006.01)

(52) U.S. Cl.
CPC .......... *A61K 38/484* (2013.01); *A61K 9/0019* (2013.01); *A61K 9/0034* (2013.01); *A61K 38/00* (2013.01); *A61P 15/02* (2018.01); *A61K 45/06* (2013.01)

(58) Field of Classification Search
CPC .... A61K 38/484; A61K 38/00; A61K 9/0034; A61K 9/0019; A61K 45/06; A61P 15/02
See application file for complete search history.

(56) References Cited

U.S. PATENT DOCUMENTS

| | | | |
|---|---|---|---|
| 3,434,929 A | 3/1969 | Buck | |
| 4,245,051 A | 1/1981 | Reich et al. | |
| 6,057,122 A | 5/2000 | Davidson | |
| 2002/0159992 A1* | 10/2002 | Henkin | A61K 38/484 424/94.63 |
| 2003/0147876 A1 | 8/2003 | Ni et al. | |
| 2004/0192640 A1* | 9/2004 | Gori | A61K 9/0034 514/53 |
| 2005/0250694 A1 | 11/2005 | Ma | |
| 2011/0142819 A1 | 6/2011 | Ny et al. | |
| 2012/0114630 A1 | 5/2012 | Zwaal | |
| 2014/0273275 A1 | 9/2014 | Jacobs et al. | |
| 2018/0360930 A1 | 12/2018 | Li | |
| 2018/0369345 A1 | 12/2018 | Li | |
| 2019/0015485 A1 | 1/2019 | Li | |
| 2019/0060420 A1 | 2/2019 | Li | |
| 2019/0083586 A1 | 3/2019 | Li | |
| 2019/0151421 A1 | 5/2019 | Li | |
| 2019/0247472 A1 | 8/2019 | Li | |

FOREIGN PATENT DOCUMENTS

| | | |
|---|---|---|
| CN | 87104683 A | 12/1988 |
| CN | 1135892 A | 11/1996 |
| CN | 1585649 A | 2/2005 |
| CN | 1768138 A | 5/2006 |
| CN | 1961958 A | 5/2007 |
| CN | 101171030 A | 4/2008 |
| CN | 101563100 A | 10/2009 |
| CN | 101573134 A | 11/2009 |
| CN | 101628113 A | 1/2010 |
| CN | 102121023 A | 7/2011 |
| CN | 103656630 A | 3/2014 |
| CN | 104914247 A | 9/2015 |
| JP | 2002512006 A | 4/2002 |
| JP | 2005519992 A | 7/2005 |
| JP | 2005525798 A | 9/2005 |
| JP | 2009502985 A | 1/2009 |
| JP | 2010502600 A | 1/2010 |
| JP | 2015505326 A | 2/2015 |
| WO | 00/18436 A1 | 4/2000 |
| WO | 2007009382 A1 | 1/2007 |
| WO | 2008026999 A2 | 3/2008 |
| WO | 2008117767 A1 | 10/2008 |
| WO | 2009093540 A1 | 7/2009 |
| WO | 2003066842 A3 | 8/2013 |
| WO | 2015026494 A2 | 2/2015 |
| WO | 2017/101866 A1 | 6/2017 |
| WO | 2017/101867 A1 | 6/2017 |
| WO | 2017/101868 A1 | 6/2017 |
| WO | 2017/101869 A1 | 6/2017 |
| WO | 2017/101870 A1 | 6/2017 |
| WO | 2017/101871 A1 | 6/2017 |
| WO | 2017/101872 A1 | 6/2017 |
| WO | 2017/101873 A1 | 6/2017 |

OTHER PUBLICATIONS

Score Search results, conducred on Jan. 15, 2020, 3 pages of PDF.*
Rijken et al., Thrombosis Research, 2001, vol. 103, p. S41-S49.*
Andreasen, P. et al., "The Urokinase-Type Plasminogen Activator System in Cancer Metastasis: A review:," Int. J. Cancer, vol. 72: 1-22 (1997).
Cai, W et al. "The anti-angiogenesis effect of plasminogen kringle 5" Progress in Physiological Sciences, vol. 35 (2):159-162 (2004).
Collen, D. et al., "Basic and Clinical Aspects of Fibrinolysis and Thrombolysis," Blood, vol. 78 (12):3114-3124 (1991).

(Continued)

*Primary Examiner* — Kade Ariani
(74) *Attorney, Agent, or Firm* — Nelson Mullins Riley & Scarborough LLP; Jill Gorny Sloper, Esq.

(57) ABSTRACT

The present invention relates to the use of plasminogen in the treatment of cervical erosion. Compared to other existing drugs for treating cervical erosion, the plasminogen or plasmin of the present invention can promote the inflammatory repair of damaged mucosa. Therefore, plasminogen may become a novel strategy to treat cervical erosion.

11 Claims, 6 Drawing Sheets

Specification includes a Sequence Listing.

(56) References Cited

OTHER PUBLICATIONS

Collen, D. et al., "Ham-Wasserman Lecture Role of the Plasminogen System in Fibrin-Homeostasis and Tissue Remodeling," American Society of Hematology, 9 pages. (2001).
Cui, F. et al., "Role of the Molecular Pathogenetic Mechanism of Plasminogen Activator-1 (PAI-1) in Fibrostic Remodeling of Radiated Renal", Chinese Clinical Rehabiliation, vol. 7(12):1768-1769 (2003).
Davalos, D. et al., "Fibrinogen as a key regulator of inflammation in disease," Semin Immunopathol., vol. 34:43-62 (2012).
Hay, E. et al., Cell Biology of Extracellular Matrix, Second Edition, 1991, 15 pages.
He, C. et al., "Tissue cooperation in a proteolytic cascade activating human interstitial collagenase," PNAS, vol. 86: 2632-2636 (1989).
Hou, W. et al., "Preparation of Human Recombinant Kringle and Bioactivity," Hereditas, vol. 27 (4):617-622 (2005).
Hunt, J. et al., "Simplified recombinant plasmin: Production and functional comparison of a novel thrombolytic molecule with plasma-derived plasmin," Thromb Haemost., vol. 100: 413-419 (2008).
International Search Report, PCT/CN2016/110454, dated Mar. 13, 2017, 14 pages.
Jin, G.H. et al., "Combination of Human Plasminogen Kringle with Ionizing Radiation Significantly Enhances the Efficacy of Antitumor Effect", Int. J. Cancer., vol. 121: 2539-2546 (2007).
Le, J. et al. "Obstetrics and Gynecology, edition 7", People's Medical Publishing House, Jan. 31, 2008 (Jan. 31, 2008), introduction.
Li, Z. et al., "Advances in Studies on Treatment for Hepatic Fibrosis", Journal of Liaoning Medical Universty, vol. 28 (2): 46-48 (2007).
Liu, M. et al., "Plasminogen: Structure, Function and Evolution", Journal of Ocean University of China, vol. 40 (10):69-74 (2010).
Lu, X.et al. "Antitumor Activity of Recombinant K1-3 Domain of Human Plasmihogen" Amino Acids and Biotic Resources, vol. 27(2):55-57 (2005).
Marder, V.J. et al., "Direct fibrinolytic agents: biochemical attributes, preclinical foundation and clinical potential," Journal of Thrombosis and Haemostasis, vol. 8: 433-444 (2010).
Mignatti, P. et al., "Biology and chemistry of proteinases in tumor invasion," Physiol Rev., vol. 73: 161-185 (2014).
Nagai, N. et al., "Recombinant human microplasmin: production and potential therapeutic properties," Journal of Thrombosis and Haemostasis, vol. 1: 307-313 (2002).
Pohl, J., et al., "Plasminogen Deficiency Leads to Impaired Lobular Reorganization and Matrix Accumulation after Chronic Liver Injury," American Journal of Pathology, vol. 159(6):2179-2186 (2001).
Raum, D., et al., "Synthesis of Human Plasminogen by the Liver," Science, vol. 208(4447): 1036-1037 (1980).
Rifkin, D. et al., "Proteolytic control of growth factor availability," APMIS, vol. 107: 80-8 (1999).
Rifkin, D.B., "Growth factor control of extracellular proteolysis," Cell Differentiation and Development, vol. 32: 313-318 (1990).
Ryu, J-K. et al., "Blood coagulation protein fibrinogen promotes autoimmunity and demyelination via chemokine release and antigen presentation," Nature Communications, vol. 6 (8164) 15 pages (2015).
Saksela, O. et al., "Cell-Associated Plasminogen Activation: Regulation and Physiological Functions," Ann. Rev. Cell Bioi., vol. 4: 93-126 (1988).
Shen, Y. et al., "Plasminogen is a Key Proinflammatory Regulator that Accelerates the Healing of Acute and Diabetic Wounds," Blood., vol. 119 (24):5879-5887 (2012).
Sottrup-Jensen, L. et al., "Amino-acid sequence of activation cleavage site in plasminogen: Homology with "pro" part of prothrombin," PNAS, vol. 72 (7): 2577-2581 (1975).
Stoppelli, M. et al., "Differentiation-enhanced binding of the amino-human urokinase plasminogen activator to a specific receptor on U937 monocytes," PNAS, vol. 82:4939-4943 (1985).

Takamura, T. et al., "Genes for systemic vascular complications are differentially expressed in the livers of Type 2 diabetic patients," Diabetologia, vol. 47: 638-647 (2004).
Tyagi, S., "Proteinases and myocardial extracellular matrix turnover," Molecular and Cellular Biochemistry, vol. 168: 1-12 (1997).
Valvil, D. et al., "Fibrinogen, chronic obstructive pulmonary disease (COPD) and outcomes in two United States cohorts," International Journal of COPD, vol. 7, 173-182 (2012).
Vassall, J-D., et al., "A Cellular Binding Site for the Mr 55,000 Form of the Human Plasminogen Activator, Urokinase," The Journal of Cell Biology, vol. 100: 86-92 (1985).
Werb, Z. et al., Endegenous Activation of Latent Collagenase by Rheumatoid Synovial Cells, The New England Journal of Medicine, vol. 296(18): 1017-1023 (1977).
Wiman, B. et al., "Structural Relationship between "Glutamic Acid" and "Lysine" Forms of Human Plasminogen and Their Interaction with the NH,-Terminal Activation Peptide as Studied by Affinity Chromatography," Eur. J. Biochem., vol. 50: 489-494 (1975).
Xie, X. et al. "Obstetrics and Gynecology, edition 8", People's Medical Publishing House, Mar. 31, 2013 (Mar. 31, 2013), p. 256.
Yu, D. et al., "Measurements of Plasmin-Alpha2 Antiplasmin Complex in Patients with Liver Cirrhosis and Hepatocarcinoma," Laboratory Medicine and Clinic, vol. 6 (2): 92-93 (2009).
U.S. Appl. No. 16/062,389, filed Jun. 14, 2018, Jinan Li , Shenzhen.
U.S. Appl. No. 16/062,421, filed Jun. 14, 2018, Jinan Li , Shenzhen.
U.S. Appl. No. 16/063,569, Jinan Li , Shenzhen.
U.S. Appl. No. 16/063,534, Jinan Li , Shenzhen.
U.S. Appl. No. 16/062,037, Jinan Li , Shenzhen.
U.S. Appl. No. 16/062,049, Jinan Li , Shenzhen.
U.S. Appl. No. 16/062,052, Jinan Li , Shenzhen.
U.S. Appl. No. 16/062,037, filed Oct. 4, 2019, C. Borgeest.
U.S. Appl. No. 16/062,037, filed May 29, 2019, C. Borgeest.
U.S. Appl. No. 16/062,049, filed Oct. 4, 2019, C. Borgeest.
U.S. Appl. No. 16/062,049, filed May 29, 2019, C. Borgeest.
U.S. Appl. No. 16/062,052, filed Nov. 18, 2019, J. Lieb.
U.S. Appl. No. 16/062,052, filed Aug. 22, 2019, J. Lieb.
U.S. Appl. No. 16/062,389, filed Oct. 7, 2019, M. Audet.
U.S. Appl. No. 16/062,389, filed Jul. 31, 2019, M. Audet.
U.S. Appl. No. 16/062,421, filed Nov. 12, 2019, K. Ariani.
U.S. Appl. No. 16/063,534, filed Nov. 18, 2019, J. Lieb.
U.S. Appl. No. 16/063,534, filed Aug. 30, 2019, J. Lieb.
A. Richard Kitching et al, "Plasminogen and Plasminogen Activators Protect against Renal Injury in Crescentic Glomerulonephritis," J. Exp. Med, vol. 185(5):963-968 (1997).
Bezerra, J. et al., "Plasminogen deficiency leads to impaired remodeling after a toxic injury to the liver," PNAS, vol. 96(26):15143-15148 (1999).
Fisher, E.J. et al"Displacement of Tissue Bound Plasminogen by Glucose: A Possible Mechanism in the Pathogenesis of Diabetic Nephropathy," Endocrinology and Metabolism, vol. 14 (6):371-376 (1997).
Li et al., "Research Progress of Liver Fibrosis Treatment," Journal of Liaoning Medical College, vol. 28(2): 46-48 (2006).
Lyer, S. et al., "Management of radiation wounds," Indian J Plast Surg., vol. 45(2): 325-331 (2012).
Mitazaki, S. et al., "Interleukin-6 modulates oxidative stress produced during the development of cisplatin nephrotoxicity," Life Sciences, vol. 92:694-700 (2013).
Naoyuki Kawao et al., "Plasminogen Plays a Crucial Role in Bone Repair," J.Bone Miner.Res., vol. 28(7):1561-1574 (2013).
NP-000292.1, plasminogen isoform 1 precursor[*Homo sapiens*], Gen-bank, Apr. 23, 2016.
Okada, K. et al., "Binding of plasminogen to hepatocytes isolated from injured mice liver and nonparenchymal cell-dependent proliferation of hepatocytes," Blood Coagulation and Fibrinolysis, vol. 19:503-511 (2008).
Romagnuolo, R., et al., NP-000292.1, "plasminogen isoform 1 precursor," GenBank, Mar. 15, 2015.
Sima J et al., "The effect of angiostatin on vascular leakage and VEGF expression in rat retina" FEBS LETT, vol. 564 (1-2):19-23 (2004).

(56) References Cited

OTHER PUBLICATIONS

Sun, Haiou, "Mechanism of Drug Induced Kidney Injury and Clinical Manifestations thereof," J Nephrol Dialy Transplant, vol. 15(3):252-257 (2006).
Tanaka, K. et al, "Involvement of tissue line system in liver regenerating: Examination using plasminogen gene knockout mice," Journal of Japan Surgical Society, vol. 101:520, 3 pages (2000).
Vogten, J. M., et al., "Angiostatin inhibits experimental liver fibrosis in mice,", International Journal of Colorectal Disease, vol. 19(4):387-394 (2004).
Zhang, S. et al., "Therapeutic Potential of Angiostatin in Diabetic Nephropathy," Journal of the American Society of Nephrology, vol. 17(2):475-486 (2006).
Zhao L. et al."Experimental Research on Radiation Protection Mecha-nism of Interleukin-6 (IL-6)" Acta Academiae Medicinae Xuzhou, vol. 25 (1): 6-8 (2005).
U.S. Appl. No. 16/062,037, filed Mar. 23, 2020, C. Borgeest.
U.S. Appl. No. 16/062,049, filed Mar. 23, 2020, C. Borgeest.
U.S. Appl. No. 16/062,052, filed Mar. 6, 2020, J. Lieb.
U.S. Appl. No. 16/062,389, filed Apr. 2, 2020, M. Audet.
U.S. Appl. No. 16/062,421, filed Mar. 2, 2020, K. Ariani.
U.S. Appl. No. 16/063,534, filed May 11, 2020, J. Lieb.
U.S. Appl. No. 16/063,569, filed Jun. 25, 2020, T. Underdahle.
U.S. Appl. No. 16/063,569, filed Feb. 24, 2020, T. Underdahle.

* cited by examiner

SEQUENCE LISTING

```
<160> NUMBER OF SEQ ID NOS: 14

<210> SEQ ID NO 1
<211> LENGTH: 2376
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Nucleotide sequence coding for the natural
      human plasminogen(Glu-PLG,Glu-plasminogen) without the signal
      peptide

<400> SEQUENCE: 1
gagcctctgg atgactatgt gaatacccag ggggcttcac tgttcagtgt cactaagaag      60
cagctgggag caggaagtat agaagaatgt gcagcaaaat gtgaggagga cgaagaattc     120
acctgcaggg cattccaata tcacagtaaa gagcaacaat gtgtgataat ggctgaaaac     180
aggaagtcct ccataatcat taggatgaga gatgtagttt tatttgaaaa gaaagtgtat     240
ctctcagagt gcaagactgg gaatggaaag aactacagag ggacgatgtc caaaacaaaa     300
aatggcatca cctgtcaaaa atggagttcc acttctcccc acagacctag attctcacct     360
gctacacacc cctcagaggg actggaggag aactactgca ggaatccaga caacgatccg     420
cagggcccct ggtgctatac tactgatcca gaaaagagat atgactactg cgacattctt     480
gagtgtgaag aggaatgtat gcattgcagt ggagaaaact atgacggcaa aatttccaag     540
accatgtctg gactggaatg ccaggcctgg gactctcaga gcccacacgc tcatggatac     600
attccttcca aatttccaaa caagaacctg aagaagaatt actgtcgtaa ccccgatagg     660
gagctgcggc cttggtgttt caccaccgac cccaacaagc gctgggaact ttgtgacatc     720
ccccgctgca acacctcc  accatcttct ggtccacct accagtgtct gaagggaaca      780
ggtgaaaact atcgcgggaa tgtggctgtt accgtgtccg ggcacacctg tcagcactgg     840
agtgcacaga cccctcacac acataacagg acaccagaaa acttccctg caaaaatttg     900 gatgaaaact actgccgcaa tcctgacgga aaaagggccc catggtgcca tacaaccaac     960
agccaagtgc ggtgggagta ctgtaagata ccgtcctgtg actcctcccc agtatccacg    1020
```

-continued

```
gaacaattgg ctcccacagc accacctgag ctaacccctg tggtccagga ctgctaccat      1080
ggtgatggac agagctaccg aggcacatcc tccaccacca ccacaggaaa gaagtgtcag      1140
tcttggtcat ctatgacacc acaccggcac cagaagaccc cagaaaacta cccaaatgct      1200
ggcctgacaa tgaactactg caggaatcca gatgccgata aaggcccctg gtgttttacc      1260
acagacccca gcgtcaggtg ggagtactgc aacctgaaaa aatgctcagg aacagaagcg      1320
agtgttgtag cacctccgcc tgttgtcctg cttccagatg tagagactcc ttccgaagaa      1380
gactgtatgt ttgggaatgg gaaaggatac cgaggcaaga gggcgaccac tgttactggg      1440
acgccatgcc aggactgggc tgcccaggag ccccatagac acagcatttt cactccagag      1500
acaaatccac gggcgggtct ggaaaaaaat tactgccgta accctgatgg tgatgtaggt      1560
ggtccctggt gctacacgac aaatccaaga aaactttacg actactgtga tgtccctcag      1620
tgtgcggccc cttcatttga ttgtgggaag cctcaagtgg agccgaagaa atgtcctgga      1680
agggttgtag gggggtgtgt ggcccaccca cattcctggc cctggcaagt cagtcttaga      1740
acaaggtttg gaatgcactt ctgtggaggc accttgatat ccccagagtg ggtgttgact      1800
gctgcccact gcttggagaa gtccccaagg ccttcatcct acaaggtcat cctgggtgca      1860
caccaagaag tgaatctcga accgcatgtt caggaaatag aagtgtctag gctgttcttg      1920
gagcccacac gaaaagatat tgccttgcta aagctaagca gtcctgccgt catcactgac      1980
aaagtaatcc cagcttgtct gccatcccca aattatgtgg tcgctgaccg gaccgaatgt      2040
ttcatcactg gctggggaga aacccaaggt acttttggag ctggccttct caaggaagcc      2100
cagctccctg tgattgagaa taaagtgtgc aatcgctatg agtttctgaa tggaagagtc      2160
caatccaccg aactctgtgc tgggcatttg gccggaggca ctgacagttg ccagggtgac      2220
agtggaggtc ctctggtttg cttcgagaag gacaaataca ttttacaagg agtcacttct      2280
tggggtcttg gctgtgcacg ccccaataag cctggtgtct atgttcgtgt ttcaaggttt      2340
gttacttgga ttgagggagt gatgagaaat aattaa                              2376
```

<210> SEQ ID NO 2
<211> LENGTH: 791
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: Amino acid sequence of the natural human
    plasminogen(Glu-PLG,Glu-plasminogen)without the
    signal peptide

<400> SEQUENCE: 2

```
Glu Pro Leu Asp Asp Tyr Val Asn Thr Gln Gly Ala Ser Leu Phe Ser
1               5                   10                  15

Val Thr Lys Lys Gln Leu Gly Ala Gly Ser Ile Glu Glu Cys Ala Ala
            20                  25                  30

Lys Cys Glu Glu Asp Glu Glu Phe Thr Cys Arg Ala Phe Gln Tyr His
        35                  40                  45

Ser Lys Glu Gln Gln Cys Val Ile Met Ala Glu Asn Arg Lys Ser Ser
    50                  55                  60

Ile Ile Ile Arg Met Arg Asp Val Val Leu Phe Glu Lys Lys Val Tyr
65                  70                  75                  80

Leu Ser Glu Cys Lys Thr Gly Asn Gly Lys Asn Tyr Arg Gly Thr Met
                85                  90                  95
```

```
Ser Lys Thr Lys Asn Gly Ile Thr Cys Gln Lys Trp Ser Ser Thr Ser
            100                 105                 110

Pro His Arg Pro Arg Phe Ser Pro Ala Thr His Pro Ser Glu Gly Leu
        115                 120                 125

Glu Glu Asn Tyr Cys Arg Asn Pro Asp Asn Asp Pro Gln Gly Pro Trp
    130                 135                 140

Cys Tyr Thr Thr Asp Pro Glu Lys Arg Tyr Asp Tyr Cys Asp Ile Leu
145                 150                 155                 160

Glu Cys Glu Glu Glu Cys Met His Cys Ser Gly Glu Asn Tyr Asp Gly
                165                 170                 175

Lys Ile Ser Lys Thr Met Ser Gly Leu Glu Cys Gln Ala Trp Asp Ser
            180                 185                 190

Gln Ser Pro His Ala His Gly Tyr Ile Pro Ser Lys Phe Pro Asn Lys
        195                 200                 205

Asn Leu Lys Lys Asn Tyr Cys Arg Asn Pro Asp Arg Glu Leu Arg Pro
    210                 215                 220

Trp Cys Phe Thr Thr Asp Pro Asn Lys Arg Trp Glu Leu Cys Asp Ile
225                 230                 235                 240

Pro Arg Cys Thr Thr Pro Pro Ser Ser Gly Pro Thr Tyr Gln Cys
                245                 250                 255

Leu Lys Gly Thr Gly Glu Asn Tyr Arg Gly Asn Val Ala Val Thr Val
            260                 265                 270

Ser Gly His Thr Cys Gln His Trp Ser Ala Gln Thr Pro His Thr His
        275                 280                 285

Asn Arg Thr Pro Glu Asn Phe Pro Cys Lys Asn Leu Asp Glu Asn Tyr
    290                 295                 300

Cys Arg Asn Pro Asp Gly Lys Arg Ala Pro Trp Cys His Thr Thr Asn
305                 310                 315                 320

Ser Gln Val Arg Trp Glu Tyr Cys Lys Ile Pro Ser Cys Asp Ser Ser
                325                 330                 335

Pro Val Ser Thr Glu Gln Leu Ala Pro Thr Ala Pro Pro Glu Leu Thr
            340                 345                 350

Pro Val Val Gln Asp Cys Tyr His Gly Asp Gly Gln Ser Tyr Arg Gly
        355                 360                 365

Thr Ser Ser Thr Thr Thr Thr Gly Lys Lys Cys Gln Ser Trp Ser Ser
    370                 375                 380

Met Thr Pro His Arg His Gln Lys Thr Pro Glu Asn Tyr Pro Asn Ala
385                 390                 395                 400

Gly Leu Thr Met Asn Tyr Cys Arg Asn Pro Asp Ala Asp Lys Gly Pro
                405                 410                 415

Trp Cys Phe Thr Thr Asp Pro Ser Val Arg Trp Glu Tyr Cys Asn Leu
            420                 425                 430

Lys Lys Cys Ser Gly Thr Glu Ala Ser Val Val Ala Pro Pro Pro Val
        435                 440                 445

Val Leu Leu Pro Asp Val Glu Thr Pro Ser Glu Glu Asp Cys Met Phe
    450                 455                 460

Gly Asn Gly Lys Gly Tyr Arg Gly Lys Arg Ala Thr Thr Val Thr Gly
465                 470                 475                 480

Thr Pro Cys Gln Asp Trp Ala Ala Gln Glu Pro His Arg His Ser Ile
                485                 490                 495

Phe Thr Pro Glu Thr Asn Pro Arg Ala Gly Leu Glu Lys Asn Tyr Cys
            500                 505                 510
```

```
Arg Asn Pro Asp Gly Asp Val Gly Gly Pro Trp Cys Tyr Thr Thr Asn
            515                 520                 525

Pro Arg Lys Leu Tyr Asp Tyr Cys Asp Val Pro Gln Cys Ala Ala Pro
    530                 535                 540

Ser Phe Asp Cys Gly Lys Pro Gln Val Glu Pro Lys Lys Cys Pro Gly
545                 550                 555                 560

Arg Val Val Gly Gly Cys Val Ala His Pro His Ser Trp Pro Trp Gln
                565                 570                 575

Val Ser Leu Arg Thr Arg Phe Gly Met His Phe Cys Gly Gly Thr Leu
            580                 585                 590

Ile Ser Pro Glu Trp Val Leu Thr Ala Ala His Cys Leu Glu Lys Ser
        595                 600                 605

Pro Arg Pro Ser Ser Tyr Lys Val Ile Leu Gly Ala His Gln Glu Val
    610                 615                 620

Asn Leu Glu Pro His Val Gln Glu Ile Glu Val Ser Arg Leu Phe Leu
625                 630                 635                 640

Glu Pro Thr Arg Lys Asp Ile Ala Leu Leu Lys Leu Ser Ser Pro Ala
                645                 650                 655

Val Ile Thr Asp Lys Val Ile Pro Ala Cys Leu Pro Ser Pro Asn Tyr
            660                 665                 670

Val Val Ala Asp Arg Thr Glu Cys Phe Ile Thr Gly Trp Gly Glu Thr
        675                 680                 685

Gln Gly Thr Phe Gly Ala Gly Leu Leu Lys Glu Ala Gln Leu Pro Val
    690                 695                 700

Ile Glu Asn Lys Val Cys Asn Arg Tyr Glu Phe Leu Asn Gly Arg Val
705                 710                 715                 720

Gln Ser Thr Glu Leu Cys Ala Gly His Leu Ala Gly Gly Thr Asp Ser
                725                 730                 735

Cys Gln Gly Asp Ser Gly Gly Pro Leu Val Cys Phe Glu Lys Asp Lys
            740                 745                 750

Tyr Ile Leu Gln Gly Val Thr Ser Trp Gly Leu Gly Cys Ala Arg Pro
        755                 760                 765

Asn Lys Pro Gly Val Tyr Val Arg Val Ser Arg Phe Val Thr Trp Ile
    770                 775                 780

Glu Gly Val Met Arg Asn Asn
785                 790

<210> SEQ ID NO 3
<211> LENGTH: 2433
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Nucleotide sequence coding for the natural
      plasminogen (from swiss prot)with the signal peptide

<400> SEQUENCE: 3
atggaacata aggaagtggt tcttctactt ctttttattc tgaaatcagg tcaaggagag      60
cctctggatg actatgtgaa tacccagggg gcttcactgt tcagtgtcac taagaagcag     120
ctgggagcag gaagtataga agaatgtgca gcaaaatgtg aggaggacga agaattcacc     180
tgcagggcat tccaatatca cagtaaagag caacaatgtg tgataatggc tgaaaacagg     240
aagtcctcca atatcattag gatgagagat gtagttttat ttgaaaagaa agtgtatctc     300
tcagagtgca agactgggaa tggaaagaac tacagaggga cgatgtccaa acaaaaaaat     360
```

```
ggcatcacct gtcaaaaatg gagttccact tctccccaca gacctagatt ctcacctgct    420
acacacccct cagagggact ggaggagaac tactgcagga atccagacaa cgatccgcag    480
gggccctggt gctatactac tgatccagaa aagagatatg actactgcga cattcttgag    540
tgtgaagagg aatgtatgca ttgcagtgga gaaaactatg acggcaaaat ttccaagacc    600
atgtctggac tggaatgcca ggcctgggac tctcagagcc cacacgctca tggatacatt    660
ccttccaaat ttccaaacaa gaacctgaag aagaattact gtcgtaaccc cgatagggag    720
ctgcggcctt ggtgtttcac caccgacccc aacaagcgct gggaactttg tgacatcccc    780
cgctgcacaa cacctccacc atcttctggt cccacctacc agtgtctgaa gggaacaggt    840
gaaaactatc gcgggaatgt ggctgttacc gtgtccgggc acacctgtca gcactggagt    900
gcacagaccc ctcacacaca taacaggaca ccagaaaact tcccctgcaa aaatttggat    960
gaaaactact gccgcaatcc tgacggaaaa agggccccat ggtgccatac aaccaacagc   1020
caagtgcggt gggagtactg taagataccg tcctgtgact cctccccagt atccacggaa   1080
caattggctc ccacagcacc acctgagcta accctgtgg tccaggactg ctaccatggt    1140
gatggacaga gctaccgagg cacatcctcc accaccacca caggaaagaa gtgtcagtct   1200
tggtcatcta tgacaccaca ccggcaccag aagacccca aaaactaccc aaatgctggc    1260
ctgacaatga actactgcag gaatccagat gccgataaag cccctggtg ttttaccaca    1320
gaccccagcg tcaggtggga gtactgcaac ctgaaaaaat gctcaggaac agaagcgagt   1380
gttgtagcac ctccgcctgt tgtcctgctt ccagatgtag agactccttc gaagaagac    1440
tgtatgtttg gaatgggaa aggataccga ggcaagaggg cgaccactgt tactgggacg   1500
ccatgccagg actgggctgc ccaggagccc catagacaca gcattttcac tccagagaca   1560
aatccacggg cggtctgga aaaaaattac tgccgtaacc ctgatggtga tgtaggtggt   1620
ccctggtgct acacgacaaa tccaagaaaa ctttacgact actgtgatgt ccctcagtgt   1680
gcggcccctt catttgattg tgggaagcct caagtggagc cgaagaaatg tcctggaagg   1740
gttgtagggg ggtgtgtggc ccacccacat tcctggccct ggcaagtcag tcttagaaca   1800
aggtttggaa tgcacttctg tggaggcacc ttgatatccc cagagtgggt gttgactgct   1860
gcccactgct tggagaagtc cccaaggcct tcatcctaca aggtcatcct gggtgcacac   1920
caagaagtga atctcgaacc gcatgttcag gaaatagaag tgtctaggct gttcttggag   1980
cccacacgaa aagatattgc cttgctaaag ctaagcagtc ctgccgtcat cactgacaaa   2040
gtaatcccag cttgtctgcc atccccaaat tatgtggtcg ctgaccggac cgaatgtttc   2100
atcactggct ggggagaaac ccaaggtact ttggagctg gccttctcaa ggaagcccag   2160
ctccctgtga ttgagaataa agtgtgcaat cgctatgagt ttctgaatgg aagagtccaa   2220
tccaccgaac tctgtgctgg gcatttggcc ggaggcactg acagttgcca gggtgacagt   2280
ggaggtcctc tggtttgctt cgagaaggac aaatacattt tacaaggagt cacttcttgg   2340
ggtcttggct gtgcacgccc caataagcct ggtgtctatg ttcgtgtttc aaggtttgtt   2400
acttggattg agggagtgat gagaaataat taa                                2433
```

<210> SEQ ID NO 4
<211> LENGTH: 810
<212> TYPE: PRT
<213> ORGANISM: Artificial Sequence
<220> FEATURE:
<223> OTHER INFORMATION: Description of Artificial Sequence: Synthetic
    polypeptide -continued <220> FEATURE:
<223> OTHER INFORMATION: Amino acid sequence coding for the natural
      plasminogen (from swiss prot) with the signal peptide

<400> SEQUENCE: 4

```
Met Glu His Lys Glu Val Val Leu Leu Leu Leu Phe Leu Lys Ser
1               5                   10                  15

Gly Gln Gly Glu Pro Leu Asp Asp Tyr Val Asn Thr Gln Gly Ala Ser
            20                  25                  30

Leu Phe Ser Val Thr Lys Lys Gln Leu Gly Ala Gly Ser Ile Glu Glu
                35                  40                  45

Cys Ala Ala Lys Cys Glu Glu Asp Glu Glu Phe Thr Cys Arg Ala Phe
50                  55                  60

Gln Tyr His Ser Lys Glu Gln Gln Cys Val Ile Met Ala Glu Asn Arg
65                  70                  75                  80

Lys Ser Ser Ile Ile Ile Arg Met Arg Asp Val Val Leu Phe Glu Lys
                85                  90                  95

Lys Val Tyr Leu Ser Glu Cys Lys Thr Gly Asn Gly Lys Asn Tyr Arg
            100                 105                 110

Gly Thr Met Ser Lys Thr Lys Asn Gly Ile Thr Cys Gln Lys Trp Ser
                115                 120                 125

Ser Thr Ser Pro His Arg Pro Arg Phe Ser Pro Ala Thr His Pro Ser
            130                 135                 140

Glu Gly Leu Glu Glu Asn Tyr Cys Arg Asn Pro Asp Asn Asp Pro Gln
145                 150                 155                 160

Gly Pro Trp Cys Tyr Thr Thr Asp Pro Glu Lys Arg Tyr Asp Tyr Cys
                165                 170                 175

Asp Ile Leu Glu Cys Glu Glu Glu Cys Met His Cys Ser Gly Glu Asn
            180                 185                 190

Tyr Asp Gly Lys Ile Ser Lys Thr Met Ser Gly Leu Glu Cys Gln Ala
                195                 200                 205

Trp Asp Ser Gln Ser Pro His Ala His Gly Tyr Ile Pro Ser Lys Phe
210                 215                 220

Pro Asn Lys Asn Leu Lys Lys Asn Tyr Cys Arg Asn Pro Asp Arg Glu
225                 230                 235                 240

Leu Arg Pro Trp Cys Phe Thr Thr Asp Pro Asn Lys Arg Trp Glu Leu
                245                 250                 255

Cys Asp Ile Pro Arg Cys Thr Thr Pro Pro Pro Ser Ser Gly Pro Thr
            260                 265                 270

Tyr Gln Cys Leu Lys Gly Thr Gly Glu Asn Tyr Arg Gly Asn Val Ala
                275                 280                 285

Val Thr Val Ser Gly His Thr Cys Gln His Trp Ser Ala Gln Thr Pro
            290                 295                 300

His Thr His Asn Arg Thr Pro Glu Asn Phe Pro Cys Lys Asn Leu Asp
305                 310                 315                 320

Glu Asn Tyr Cys Arg Asn Pro Asp Gly Lys Arg Ala Pro Trp Cys His
                325                 330                 335

Thr Thr Asn Ser Gln Val Arg Trp Glu Tyr Cys Lys Ile Pro Ser Cys
            340                 345                 350

Asp Ser Ser Pro Val Ser Thr Glu Gln Leu Ala Pro Thr Ala Pro Pro
                355                 360                 365
```

```
Glu Leu Thr Pro Val Val Gln Asp Cys Tyr His Gly Asp Gly Gln Ser
370                 375                 380

Tyr Arg Gly Thr Ser Ser Thr Thr Thr Thr Gly Lys Lys Cys Gln Ser
385                 390                 395                 400

Trp Ser Ser Met Thr Pro His Arg His Gln Lys Thr Pro Glu Asn Tyr
                405                 410                 415

Pro Asn Ala Gly Leu Thr Met Asn Tyr Cys Arg Asn Pro Asp Ala Asp
                420                 425                 430

Lys Gly Pro Trp Cys Phe Thr Thr Asp Pro Ser Val Arg Trp Glu Tyr
            435                 440                 445

Cys Asn Leu Lys Lys Cys Ser Gly Thr Glu Ala Ser Val Val Ala Pro
450                 455                 460

Pro Pro Val Val Leu Leu Pro Asp Val Glu Thr Pro Ser Glu Glu Asp
465                 470                 475                 480

Cys Met Phe Gly Asn Gly Lys Gly Tyr Arg Gly Lys Arg Ala Thr Thr
                485                 490                 495

Val Thr Gly Thr Pro Cys Gln Asp Trp Ala Ala Gln Glu Pro His Arg
                500                 505                 510

His Ser Ile Phe Thr Pro Glu Thr Asn Pro Arg Ala Gly Leu Glu Lys
            515                 520                 525

Asn Tyr Cys Arg Asn Pro Asp Gly Asp Val Gly Gly Pro Trp Cys Tyr
530                 535                 540

Thr Thr Asn Pro Arg Lys Leu Tyr Asp Tyr Cys Asp Val Pro Gln Cys
545                 550                 555                 560

Ala Ala Pro Ser Phe Asp Cys Gly Lys Pro Gln Val Glu Pro Lys Lys
                565                 570                 575

Cys Pro Gly Arg Val Val Gly Gly Cys Val Ala His Pro His Ser Trp
                580                 585                 590

Pro Trp Gln Val Ser Leu Arg Thr Arg Phe Gly Met His Phe Cys Gly
            595                 600                 605

Gly Thr Leu Ile Ser Pro Glu Trp Val Leu Thr Ala Ala His Cys Leu
            610                 615                 620

Glu Lys Ser Pro Arg Pro Ser Ser Tyr Lys Val Ile Leu Gly Ala His
625                 630                 635                 640

Gln Glu Val Asn Leu Glu Pro His Val Gln Glu Ile Glu Val Ser Arg
                645                 650                 655

Leu Phe Leu Glu Pro Thr Arg Lys Asp Ile Ala Leu Leu Lys Leu Ser
                660                 665                 670

Ser Pro Ala Val Ile Thr Asp Lys Val Ile Pro Ala Cys Leu Pro Ser
                675                 680                 685

Pro Asn Tyr Val Val Ala Asp Arg Thr Glu Cys Phe Ile Thr Gly Trp
                690                 695                 700

Gly Glu Thr Gln Gly Thr Phe Gly Ala Gly Leu Leu Lys Glu Ala Gln
705                 710                 715                 720

Leu Pro Val Ile Glu Asn Lys Val Cys Asn Arg Tyr Glu Phe Leu Asn
                725                 730                 735

Gly Arg Val Gln Ser Thr Glu Leu Cys Ala Gly His Leu Ala Gly Gly
                740                 745                 750

Thr Asp Ser Cys Gln Gly Asp Ser Gly Gly Pro Leu Val Cys Phe Glu
            755                 760                 765

Lys Asp Lys Tyr Ile Leu Gln Gly Val Thr Ser Trp Gly Leu Gly Cys
770                 775                 780
```

```
Ala Arg Pro Asn Lys Pro Gly Val Tyr Val Arg Val Ser Arg Phe Val
785                 790                 795                 800

Thr Trp Ile Glu Gly Val Met Arg Asn Asn
                805                 810

<210> SEQ ID NO 5
<211> LENGTH: 2145
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Nucleotide sequence coding for
      LYS77-PLG(Lys-plasminogen)

<400> SEQUENCE: 5
aaagtgtatc tctcagagtg caagactggg aatggaaaga actacagagg gacgatgtcc      60
aaaacaaaaa atggcatcac ctgtcaaaaa tggagttcca cttctcccca cagacctaga     120
ttctcacctg ctacacaccc ctcagaggga ctggaggaga actactgcag gaatccagac     180
aacgatccgc aggggccctg gtgctatact actgatccag aaaagagata tgactactgc     240
gacattcttg agtgtgaaga ggaatgtatg cattgcagtg gagaaaacta tgacggcaaa     300
atttccaaga ccatgtctgg actggaatgc caggcctggg actctcagag cccacacgct     360
catggataca ttccttccaa atttccaaac aagaacctga aagaattact gtcgtaac       420 cccgataggg agctgcggcc ttggtgtttc accaccgacc caacaagcg ctgggaactt      480 tgtgacatcc cccgctgcac aacacctcca ccatcttctg gtcccaccta ccagtgtctg     540
aagggaacag gtgaaaacta cgcgggaat gtggctgtta ccgtgtccgg gcacacctgt     600
cagcactgga gtgcacagac ccctcacaca cataacagga caccagaaaa cttcccctgc     660
aaaaatttgg atgaaaacta ctgccgcaat cctgacggaa aaagggcccc atggtgccat     720
acaaccaaca gccaagtgcg gtgggagtac tgtaagatac cgtcctgtga ctcctcccca     780
gtatccacgg aacaattggc tcccacagca ccacctgagc taaccccctgt ggtccaggac     840 tgctaccatg gtgatggaca gagctaccga ggcacatcct ccaccaccac cacaggaaag     900
aagtgtcagt cttggtcatc tatgacacca caccggcacc agaagacccc agaaaactac     960
ccaaatgctg gcctgacaat gaactactgc aggaatccag atgccgataa aggcccctgg    1020
tgttttacca cagaccccag cgtcaggtgg gagtactgca acctgaaaaa atgctcagga    1080
acagaagcga gtgttgtagc acctccgcct gttgtcctgc ttccagatgt agagactcct    1140
tccgaagaag actgtatgtt tgggaatggg aaaggatacc gaggcaagag ggcgaccact    1200
gttactggga cgccatgcca ggactgggct gcccaggagc ccatagaca cagcattttc    1260 actccagaga caaatccacg ggcgggtctg gaaaaaaatt actgccgtaa ccctgatggt    1320
gatgtaggtg gtccctggtg ctacacgaca aatccaagaa aactttacga ctactgtgat    1380
gtccctcagt gtgcggcccc ttcatttgat tgtgggaagc tcaagtgga gccgaagaaa    1440 tgtcctggaa gggttgtagg ggggtgtgtg gcccacccac attcctggcc ctggcaagtc    1500
agtcttagaa caaggtttgg aatgcacttc tgtggaggca ccttgatatc cccagagtgg    1560
gtgttgactg ctgcccactg cttggagaag tccccaaggc cttcatccta caaggtcatc    1620
ctgggtgcac accaagaagt gaatctcgaa ccgcatgttc aggaaataga agtgtctagg    1680
ctgttcttgg agcccacacg aaaagatatt gccttgctaa agctaagcag tcctgccgtc    1740
atcactgaca aagtaatccc agcttgtctg ccatccccaa attatgtggt cgctgaccgg    1800
```

-continued

```
accgaatgtt tcatcactgg ctggggagaa acccaaggta cttttggagc tggccttctc    1860
aaggaagccc agctccctgt gattgagaat aaagtgtgca atcgctatga gtttctgaat    1920
ggaagagtcc aatccaccga actctgtgct gggcatttgg ccggaggcac tgacagttgc    1980
cagggtgaca gtggaggtcc tctggtttgc ttcgagaagg acaaatacat tttacaagga    2040
gtcacttctt ggggtcttgg ctgtgcacgc cccaataagc ctggtgtcta tgttcgtgtt    2100
tcaaggtttg ttacttggat tgagggagtg atgagaaata attaa                   2145
```

<210> SEQ ID NO 6
<211> LENGTH: 714
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequence of
      LYS77-PLG(Lys-plasminogen)

<400> SEQUENCE: 6

```
Lys Val Tyr Leu Ser Glu Cys Lys Thr Gly Asn Gly Lys Asn Tyr Arg
1               5                   10                  15

Gly Thr Met Ser Lys Thr Lys Asn Gly Ile Thr Cys Gln Lys Trp Ser
            20                  25                  30

Ser Thr Ser Pro His Arg Pro Arg Phe Ser Pro Ala Thr His Pro Ser
        35                  40                  45

Glu Gly Leu Glu Glu Asn Tyr Cys Arg Asn Pro Asp Asn Asp Pro Gln
    50                  55                  60

Gly Pro Trp Cys Tyr Thr Thr Asp Pro Glu Lys Arg Tyr Asp Tyr Cys
65                  70                  75                  80

Asp Ile Leu Glu Cys Glu Glu Cys Met His Cys Ser Gly Glu Asn
                85                  90                  95

Tyr Asp Gly Lys Ile Ser Lys Thr Met Ser Gly Leu Glu Cys Gln Ala
            100                 105                 110

Trp Asp Ser Gln Ser Pro His Ala His Gly Tyr Ile Pro Ser Lys Phe
        115                 120                 125

Pro Asn Lys Asn Leu Lys Lys Asn Tyr Cys Arg Asn Pro Asp Arg Glu
    130                 135                 140

Leu Arg Pro Trp Cys Phe Thr Thr Asp Pro Asn Lys Arg Trp Glu Leu
145                 150                 155                 160

Cys Asp Ile Pro Arg Cys Thr Thr Pro Pro Ser Ser Gly Pro Thr
                165                 170                 175

Tyr Gln Cys Leu Lys Gly Thr Gly Glu Asn Tyr Arg Gly Asn Val Ala
            180                 185                 190

Val Thr Val Ser Gly His Thr Cys Gln His Trp Ser Ala Gln Thr Pro
        195                 200                 205

His Thr His Asn Arg Thr Pro Glu Asn Phe Pro Cys Lys Asn Leu Asp
    210                 215                 220

Glu Asn Tyr Cys Arg Asn Pro Asp Gly Lys Arg Ala Pro Trp Cys His
225                 230                 235                 240

Thr Thr Asn Ser Gln Val Arg Trp Glu Tyr Cys Lys Ile Pro Ser Cys
                245                 250                 255

Asp Ser Ser Pro Val Ser Thr Glu Gln Leu Ala Pro Thr Ala Pro Pro
            260                 265                 270

Glu Leu Thr Pro Val Val Gln Asp Cys Tyr His Gly Asp Gly Gln Ser
        275                 280                 285
```

-continued

```
Tyr Arg Gly Thr Ser Ser Thr Thr Thr Gly Lys Lys Cys Gln Ser
    290                 295                 300

Trp Ser Ser Met Thr Pro His Arg His Gln Lys Thr Pro Glu Asn Tyr
305                 310                 315                 320

Pro Asn Ala Gly Leu Thr Met Asn Tyr Cys Arg Asn Pro Asp Ala Asp
                325                 330                 335

Lys Gly Pro Trp Cys Phe Thr Thr Asp Pro Ser Val Arg Trp Glu Tyr
            340                 345                 350

Cys Asn Leu Lys Lys Cys Ser Gly Thr Glu Ala Ser Val Val Ala Pro
        355                 360                 365

Pro Pro Val Val Leu Leu Pro Asp Val Glu Thr Pro Ser Glu Glu Asp
370                 375                 380

Cys Met Phe Gly Asn Gly Lys Gly Tyr Arg Gly Lys Arg Ala Thr Thr
385                 390                 395                 400

Val Thr Gly Thr Pro Cys Gln Asp Trp Ala Ala Gln Glu Pro His Arg
                405                 410                 415

His Ser Ile Phe Thr Pro Glu Thr Asn Pro Arg Ala Gly Leu Glu Lys
            420                 425                 430

Asn Tyr Cys Arg Asn Pro Asp Gly Asp Val Gly Gly Pro Trp Cys Tyr
        435                 440                 445

Thr Thr Asn Pro Arg Lys Leu Tyr Asp Tyr Cys Asp Val Pro Gln Cys
    450                 455                 460

Ala Ala Pro Ser Phe Asp Cys Gly Lys Pro Gln Val Glu Pro Lys Lys
465                 470                 475                 480

Cys Pro Gly Arg Val Val Gly Gly Cys Val Ala His Pro His Ser Trp
                485                 490                 495

Pro Trp Gln Val Ser Leu Arg Thr Arg Phe Gly Met His Phe Cys Gly
            500                 505                 510

Gly Thr Leu Ile Ser Pro Glu Trp Val Leu Thr Ala Ala His Cys Leu
        515                 520                 525

Glu Lys Ser Pro Arg Pro Ser Ser Tyr Lys Val Ile Leu Gly Ala His
    530                 535                 540

Gln Glu Val Asn Leu Glu Pro His Val Gln Glu Ile Glu Val Ser Arg
545                 550                 555                 560

Leu Phe Leu Glu Pro Thr Arg Lys Asp Ile Ala Leu Leu Lys Leu Ser
                565                 570                 575

Ser Pro Ala Val Ile Thr Asp Lys Val Ile Pro Ala Cys Leu Pro Ser
            580                 585                 590

Pro Asn Tyr Val Val Ala Asp Arg Thr Glu Cys Phe Ile Thr Gly Trp
        595                 600                 605

Gly Glu Thr Gln Gly Thr Phe Gly Ala Gly Leu Leu Lys Glu Ala Gln
    610                 615                 620

Leu Pro Val Ile Glu Asn Lys Val Cys Asn Arg Tyr Glu Phe Leu Asn
625                 630                 635                 640

Gly Arg Val Gln Ser Thr Glu Leu Cys Ala Gly His Leu Ala Gly Gly
                645                 650                 655

Thr Asp Ser Cys Gln Gly Asp Ser Gly Gly Pro Leu Val Cys Phe Glu
            660                 665                 670

Lys Asp Lys Tyr Ile Leu Gln Gly Val Thr Ser Trp Gly Leu Gly Cys
        675                 680                 685
```

Ala Arg Pro Asn Lys Pro Gly Val Tyr Val Arg Val Ser Arg Phe Val
      690                 695                 700

Thr Trp Ile Glu Gly Val Met Arg Asn Asn
705                 710

<210> SEQ ID NO 7
<211> LENGTH: 1245
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Nucleotide sequence coding for
      delta-plg(delta-plasminogen)

<400> SEQUENCE: 7
gagcctctgg atgactatgt gaatacccag ggggcttcac tgttcagtgt cactaagaag    60
cagctgggag caggaagtat agaagaatgt gcagcaaaat gtgaggagga cgaagaattc   120
acctgcaggg cattccaata tcacagtaaa gagcaacaat gtgtgataat ggctgaaaac   180
aggaagtcct ccataatcat taggatgaga gatgtagttt tatttgaaaa gaaagtgtat   240
ctctcagagt gcaagactgg gaatggaaag aactacagag ggacgatgtc caaaacaaaa   300
aatggcatca cctgtcaaaa atggagttcc acttctcccc acagacctag attctcacct   360
gctacacacc cctcagaggg actggaggag aactactgca ggaatccaga caacgatccg   420
caggggccct ggtgctatac tactgatcca gaaaagagat atgactactg cgacattctt   480
gagtgtgaag aggcggcccc ttcatttgat tgtgggaagc tcaagtggac gccgaagaaa   540
tgtcctggaa gggttgtagg ggggtgtgtg gcccacccac attcctggcc ctggcaagtc   600
agtcttagaa caaggtttgg aatgcacttc tgtggaggca ccttgatatc cccagagtgg   660
gtgttgactg ctgcccactg cttggagaag tccccaaggc cttcatccta caaggtcatc   720
ctgggtgcac accaagaagt gaatctcgaa ccgcatgttc aggaaataga agtgtctagg   780
ctgttcttgg agcccacacg aaaagatatt gccttgctaa agctaagcag tcctgccgtc   840
atcactgaca aagtaatccc agcttgtctg ccatccccaa attatgtggt cgctgaccgg   900
accgaatgtt tcatcactgg ctggggagaa acccaaggta cttttggagc tggccttctc   960
aaggaagccc agctccctgt gattgagaat aaagtgtgca atcgctatga gtttctgaat  1020
ggaagagtcc aatccaccga actctgtgct gggcatttgg ccggaggcac tgacagttgc  1080
cagggtgaca gtggaggtcc tctggttttgc ttcgagaagg acaaatacat tttacaagga  1140
gtcacttctt ggggtcttgg ctgtgcacgc cccaataagc ctggtgtcta tgttcgtgtt  1200
tcaaggtttg ttacttggat tgagggagtg atgagaaata attaa                  1245

<210> SEQ ID NO 8
<211> LENGTH: 414
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequence of
      delta-plg(delta-plasminogen)

```
<400> SEQUENCE: 8

Glu Pro Leu Asp Asp Tyr Val Asn Thr Gln Gly Ala Ser Leu Phe Ser
1               5                   10                  15

Val Thr Lys Lys Gln Leu Gly Ala Gly Ser Ile Glu Glu Cys Ala Ala
            20                  25                  30

Lys Cys Glu Glu Asp Glu Glu Phe Thr Cys Arg Ala Phe Gln Tyr His
                35                  40                  45

Ser Lys Glu Gln Gln Cys Val Ile Met Ala Glu Asn Arg Lys Ser Ser
    50                  55                  60

Ile Ile Ile Arg Met Arg Asp Val Val Leu Phe Glu Lys Lys Val Tyr
65                  70                  75                  80

Leu Ser Glu Cys Lys Thr Gly Asn Gly Lys Asn Tyr Arg Gly Thr Met
                85                  90                  95

Ser Lys Thr Lys Asn Gly Ile Thr Cys Gln Lys Trp Ser Ser Thr Ser
            100                 105                 110

Pro His Arg Pro Arg Phe Ser Pro Ala Thr His Pro Ser Glu Gly Leu
                115                 120                 125

Glu Glu Asn Tyr Cys Arg Asn Pro Asp Asn Asp Pro Gln Gly Pro Trp
    130                 135                 140

Cys Tyr Thr Thr Asp Pro Glu Lys Arg Tyr Asp Tyr Cys Asp Ile Leu
145                 150                 155                 160

Glu Cys Glu Glu Ala Ala Pro Ser Phe Asp Cys Gly Lys Pro Gln Val
                165                 170                 175

Glu Pro Lys Lys Cys Pro Gly Arg Val Val Gly Gly Cys Val Ala His
                180                 185                 190

Pro His Ser Trp Pro Trp Gln Val Ser Leu Arg Thr Arg Phe Gly Met
                195                 200                 205

His Phe Cys Gly Gly Thr Leu Ile Ser Pro Glu Trp Val Leu Thr Ala
210                 215                 220

Ala His Cys Leu Glu Lys Ser Pro Arg Pro Ser Ser Tyr Lys Val Ile
225                 230                 235                 240

Leu Gly Ala His Gln Glu Val Asn Leu Glu Pro His Val Gln Glu Ile
                245                 250                 255

Glu Val Ser Arg Leu Phe Leu Glu Pro Thr Arg Lys Asp Ile Ala Leu
                260                 265                 270

Leu Lys Leu Ser Ser Pro Ala Val Ile Thr Asp Lys Val Ile Pro Ala
            275                 280                 285

Cys Leu Pro Ser Pro Asn Tyr Val Val Ala Asp Arg Thr Glu Cys Phe
290                 295                 300

Ile Thr Gly Trp Gly Glu Thr Gln Gly Thr Phe Gly Ala Gly Leu Leu
305                 310                 315                 320

Lys Glu Ala Gln Leu Pro Val Ile Glu Asn Lys Val Cys Asn Arg Tyr
                325                 330                 335

Glu Phe Leu Asn Gly Arg Val Gln Ser Thr Glu Leu Cys Ala Gly His
                340                 345                 350

Leu Ala Gly Gly Thr Asp Ser Cys Gln Gly Asp Ser Gly Gly Pro Leu
            355                 360                 365

Val Cys Phe Glu Lys Asp Lys Tyr Ile Leu Gln Gly Val Thr Ser Trp
            370                 375                 380

Gly Leu Gly Cys Ala Arg Pro Asn Lys Pro Gly Val Tyr Val Arg Val
385                 390                 395                 400

Ser Arg Phe Val Thr Trp Ile Glu Gly Val Met Arg Asn Asn
                405                 410
```

<210> SEQ ID NO 9
<211> LENGTH: 1104
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Nucleotide sequence coding for Mini-plg(mini-plasminogen)

<400> SEQUENCE: 9

```
gtcaggtggg agtactgcaa cctgaaaaaa tgctcaggaa cagaagcgag tgttgtagca      60
cctccgcctg ttgtcctgct tccagatgta gagactcctt ccgaagaaga ctgtatgttt     120
gggaatggga aggataccg aggcaagagg gcgaccactg ttactgggac gccatgccag      180
gactgggctg cccaggagcc ccatagacac agcattttca ctccagagac aaatccacgg     240
gcgggtctgg aaaaaaatta ctgccgtaac cctgatggtg atgtaggtgg tccctggtgc     300
tacacgacaa atccaagaaa actttacgac tactgtgatg tccctcagtg tgcggcccct     360
tcatttgatt gtgggaagcc tcaagtggag ccgaagaaat gtcctggaag ggttgtaggg     420
gggtgtgtgg cccacccaca ttcctggccc tggcaagtca gtcttagaac aaggtttgga     480
atgcacttct gtggaggcac cttgatatcc ccagagtggg tgttgactgc tgcccactgc     540
ttggagaagt ccccaaggcc ttcatcctac aaggtcatcc tgggtgcaca ccaagaagtg     600
aatctcgaac cgcatgttca ggaaatagaa gtgtctaggc tgttcttgga gcccacacga     660
aaagatattg ccttgctaaa gctaagcagt cctgccgtca tcactgacaa agtaatccca     720
gcttgtctgc catccccaaa ttatgtggtc gctgaccgga ccgaatgttt catcactggc     780
tggggagaaa cccaaggtac ttttggagct ggccttctca aggaagccca gctccctgtg     840
attgagaata aagtgtgcaa tcgctatgag tttctgaatg gaagagtcca atccaccgaa     900
ctctgtgctg gcattttggc cggaggcact gacagttgcc agggtgacag tggaggtcct     960
ctggtttgct tcgagaagga caaatacatt ttacaaggag tcacttcttg gggtcttggc    1020
tgtgcacgcc ccaataagcc tggtgtctat gttcgtgttt caaggtttgt tacttggatt    1080
gagggagtga tgagaaataa ttaa                                           1104
```

<210> SEQ ID NO 10
<211> LENGTH: 367
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Amino acid sequence of Mini-plg(mini-plasminogen)

<400> SEQUENCE: 10

Val Arg Trp Glu Tyr Cys Asn Leu Lys Lys Cys Ser Gly Thr Glu Ala
1               5                  10                  15

Ser Val Val Ala Pro Pro Val Val Leu Leu Pro Asp Val Glu Thr
            20                  25                  30

Pro Ser Glu Glu Asp Cys Met Phe Gly Asn Gly Lys Gly Tyr Arg Gly
        35                  40                  45

Lys Arg Ala Thr Thr Val Thr Gly Thr Pro Cys Gln Asp Trp Ala Ala
    50                  55                  60

Gln Glu Pro His Arg His Ser Ile Phe Thr Pro Glu Thr Asn Pro Arg
65                  70                  75                  80

```
Ala Gly Leu Glu Lys Asn Tyr Cys Arg Asn Pro Asp Gly Asp Val Gly
            85                  90                  95

Gly Pro Trp Cys Tyr Thr Thr Asn Pro Arg Lys Leu Tyr Asp Tyr Cys
            100                 105                 110

Asp Val Pro Gln Cys Ala Ala Pro Ser Phe Asp Cys Gly Lys Pro Gln
            115                 120                 125

Val Glu Pro Lys Lys Cys Pro Gly Arg Val Val Gly Gly Cys Val Ala
            130                 135                 140

His Pro His Ser Trp Pro Trp Gln Val Ser Leu Arg Thr Arg Phe Gly
145                 150                 155                 160

Met His Phe Cys Gly Gly Thr Leu Ile Ser Pro Glu Trp Val Leu Thr
            165                 170                 175

Ala Ala His Cys Leu Glu Lys Ser Pro Arg Pro Ser Ser Tyr Lys Val
            180                 185                 190

Ile Leu Gly Ala His Gln Glu Val Asn Leu Glu Pro His Val Gln Glu
            195                 200                 205

Ile Glu Val Ser Arg Leu Phe Leu Glu Pro Thr Arg Lys Asp Ile Ala
            210                 215                 220

Leu Leu Lys Leu Ser Ser Pro Ala Val Ile Thr Asp Lys Val Ile Pro
225                 230                 235                 240

Ala Cys Leu Pro Ser Pro Asn Tyr Val Val Ala Asp Arg Thr Glu Cys
            245                 250                 255

Phe Ile Thr Gly Trp Gly Glu Thr Gln Gly Thr Phe Gly Ala Gly Leu
            260                 265                 270

Leu Lys Glu Ala Gln Leu Pro Val Ile Glu Asn Lys Val Cys Asn Arg
            275                 280                 285

Tyr Glu Phe Leu Asn Gly Arg Val Gln Ser Thr Glu Leu Cys Ala Gly
            290                 295                 300

His Leu Ala Gly Gly Thr Asp Ser Cys Gln Gly Asp Ser Gly Gly Pro
305                 310                 315                 320

Leu Val Cys Phe Glu Lys Asp Lys Tyr Ile Leu Gln Gly Val Thr Ser
            325                 330                 335

Trp Gly Leu Gly Cys Ala Arg Pro Asn Lys Pro Gly Val Tyr Val Arg
            340                 345                 350

Val Ser Arg Phe Val Thr Trp Ile Glu Gly Val Met Arg Asn Asn
            355                 360                 365

<210> SEQ ID NO 11
<211> LENGTH: 750
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Nucleotide sequence coding for
      Micro-plg(micro-plasminogen)

<400> SEQUENCE: 11
gccccttcat tgattgtgg gaagcctcaa gtggagccga agaaatgtcc tggaagggtt      60 gtagggggt gtgtggccca cccacattcc tggccctggc aagtcagtct tagaacaagg    120
tttggaatgc acttctgtgg aggcaccttg atatcccag agtgggtgtt gactgctgcc    180
cactgcttgg agaagtcccc aaggccttca tcctacaagg tcatcctggg tgcacaccaa    240
gaagtgaatc tcgaaccgca tgttcaggaa atagaagtgt ctaggctgtt cttggagccc    300
acacgaaaag atattgcctt gctaaagcta agcagtcctg ccgtcatcac tgacaaagta    360
```

```
atcccagctt gtctgccatc cccaaattat gtggtcgctg accggaccga atgtttcatc     420
actggctggg gagaaaccca aggtactttt ggagctggcc ttctcaagga agcccagctc     480
cctgtgattg agaataaagt gtgcaatcgc tatgagtttc tgaatggaag agtccaatcc     540
accgaactct gtgctgggca tttggccgga ggcactgaca gttgccaggg tgacagtgga     600
ggtcctctgg tttgcttcga␣gaaggacaaa tacattttac aaggagtcac ttcttggggt      660
cttggctgtg cacgccccaa taagcctggt gtctatgttc gtgtttcaag gtttgttact     720 tggattgagg␣gagtgatgag aaataattaa                                         750
```

<210> SEQ ID NO 12
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequence coding for
      Micro-plg(micro-plasminogen)

<400> SEQUENCE: 12

```
Ala Pro Ser Phe Asp Cys Gly Lys Pro Gln Val Glu Pro Lys Lys Cys
1               5                   10                  15

Pro Gly Arg Val Val Gly Gly Cys Val Ala His Pro His Ser Trp Pro
            20                  25                  30

Trp Gln Val Ser Leu Arg Thr Arg Phe Gly Met His Phe Cys Gly Gly
        35                  40                  45

Thr Leu Ile Ser Pro Glu Trp Val Leu Thr Ala Ala His Cys Leu Glu
    50                  55                  60

Lys Ser Pro Arg Pro Ser Ser Tyr Lys Val Ile Leu Gly Ala His Gln
65                  70                  75                  80

Glu Val Asn Leu Glu Pro His Val Gln Glu Ile Glu Val Ser Arg Leu
                85                  90                  95

Phe Leu Glu Pro Thr Arg Lys Asp Ile Ala Leu Leu Lys Leu Ser Ser
            100                 105                 110

Pro Ala Val Ile Thr Asp Lys Val Ile Pro Ala Cys Leu Pro Ser Pro
        115                 120                 125

Asn Tyr Val Val Ala Asp Arg Thr Glu Cys Phe Ile Thr Gly Trp Gly
    130                 135                 140

Glu Thr Gln Gly Thr Phe Gly Ala Gly Leu Leu Lys Glu Ala Gln Leu
145                 150                 155                 160

Pro Val Ile Glu Asn Lys Val Cys Asn Arg Tyr Glu Phe Leu Asn Gly
                165                 170                 175

Arg Val Gln Ser Thr Glu Leu Cys Ala Gly His Leu Ala Gly Gly Thr
            180                 185                 190

Asp Ser Cys Gln Gly Asp Ser Gly Gly Pro Leu Val Cys Phe Glu Lys
        195                 200                 205

Asp Lys Tyr Ile Leu Gln Gly Val Thr Ser Trp Gly Leu Gly Cys Ala
    210                 215                 220

Arg Pro Asn Lys Pro Gly Val Tyr Val Arg Val Ser Arg Phe Val Thr
225                 230                 235                 240

Trp Ile Glu Gly Val Met Arg Asn Asn
                245
```

<210> SEQ ID NO 13
<211> LENGTH: 684
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Nucleotide sequence coding for the serine protease domain

<400> SEQUENCE: 13

```
gttgtagggg ggtgtgtggc ccacccacat tcctggccct ggcaagtcag tcttagaaca      60
aggtttggaa tgcacttctg tggaggcacc ttgatatccc cagagtgggt gttgactgct     120
gcccactgct tggagaagtc cccaaggcct tcatcctaca aggtcatcct gggtgcacac     180
caagaagtga atctcgaacc gcatgttcag gaaatagaag tgtctaggct gttcttggag     240
cccacacgaa aagatattgc cttgctaaag ctaagcagtc ctgccgtcat cactgacaaa     300
gtaatcccag cttgtctgcc atccccaaat tatgtggtcg ctgaccggac cgaatgtttc     360
atcactggct ggggagaaac ccaaggtact tttggagctg gccttctcaa ggaagcccag     420
ctccctgtga ttgagaataa agtgtgcaat cgctatgagt ttctgaatgg aagagtccaa     480
tccaccgaac tctgtgctgg gcatttggcc ggaggcactg acagttgcca gggtgacagt     540
ggaggtcctc tggtttgctt cgagaaggac aaatacattt tacaaggagt cacttcttgg     600
ggtcttggct gtgcacgccc caataagcct ggtgtctatg ttcgtgtttc aaggtttgtt     660
acttggattg agggagtgat gaga                                            684
```

<210> SEQ ID NO 14
<211> LENGTH: 228
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Amino acid sequence coding for the serine protease domain

<400> SEQUENCE: 14

```
Val Val Gly Gly Cys Val Ala His Pro His Ser Trp Pro Trp Gln Val
1               5                   10                  15

Ser Leu Arg Thr Arg Phe Gly Met His Phe Cys Gly Gly Thr Leu Ile
            20                  25                  30

Ser Pro Glu Trp Val Leu Thr Ala Ala His Cys Leu Glu Lys Ser Pro
        35                  40                  45

Arg Pro Ser Ser Tyr Lys Val Ile Leu Gly Ala His Gln Glu Val Asn
    50                  55                  60

Leu Glu Pro His Val Gln Glu Ile Glu Val Ser Arg Leu Phe Leu Glu
65                  70                  75                  80

Pro Thr Arg Lys Asp Ile Ala Leu Leu Lys Leu Ser Ser Pro Ala Val
                85                  90                  95

Ile Thr Asp Lys Val Ile Pro Ala Cys Leu Pro Ser Pro Asn Tyr Val
            100                 105                 110

Val Ala Asp Arg Thr Glu Cys Phe Ile Thr Gly Trp Gly Glu Thr Gln
        115                 120                 125

Gly Thr Phe Gly Ala Gly Leu Leu Lys Glu Ala Gln Leu Pro Val Ile
    130                 135                 140
```

-continued

```
Glu Asn Lys Val Cys Asn Arg Tyr Glu Phe Leu Asn Gly Arg Val Gln
145                 150                 155                 160

Ser Thr Glu Leu Cys Ala Gly His Leu Ala Gly Gly Thr Asp Ser Cys
                165                 170                 175

Gln Gly Asp Ser Gly Gly Pro Leu Val Cys Phe Glu Lys Asp Lys Tyr
            180                 185                 190

Ile Leu Gln Gly Val Thr Ser Trp Gly Leu Gly Cys Ala Arg Pro Asn
        195                 200                 205

Lys Pro Gly Val Tyr Val Arg Val Ser Arg Phe Val Thr Trp Ile Glu
    210                 215                 220

Gly Val Met Arg
225
```

METHOD FOR PREVENTING AND TREATING CERVICAL EROSION

CROSS-REFERENCE TO RELATED APPLICATIONS

This application is a 35 U.S.C. 371 national stage filing of International Application No. PCT/CN2016/110454, filed on Dec. 16, 2016, which claims priority to International Application No. PCT/CN2015/097948, filed on Dec. 18, 2015. The contents of the aforementioned applications are hereby incorporated by reference in their entireties.

SEQUENCE LISTING

The instant application contains a Sequence Listing which has been submitted electronically in ASCII format and is hereby incorporated by reference in its entirety. Said ASCII copy, created on Sep. 19, 2018, is named BCLS-002US_Sequence-2.txt and is 48,326 bytes in size.

TECHNICAL FIELD

The present invention relates to a novel method for preventing and/or treating cervical erosion using plasminogen or plasmin. Compared with the conventional drugs for treating cervical erosion, this method can effectively promote the repair of damaged mucosa.

BACKGROUND

Chronic cervicitis is a common and frequently-occurring disease among married women. It takes the first place among women in China and accounts for about 50% of the gynecological diseases. Cervical erosion is also one of the most common pathological changes in chronic cervicitis. The incidence of cervical cancer is 7.3 times higher than that of women without cervical erosion. It has been reported that about 80% of isolated squamous cell carcinomas occur in the cervical canal or erosion area, i.e., the columnar epithelium, and most of them occur in the "erosion" area[1]. The main cause of cervical erosion is usually due to injury to the cervix after giving birth or surgery and the subsequent invasion of pathogens. Before the 1980s, the main pathogens causing chronic cervicitis were *Staphylococci, Streptococcus, Escherichia coli,* and anaerobes[2]. In recent years, as the incidence of sexually transmitted diseases has increased year by year and sexually transmitted diseases have increased, cervical erosion has also shown an increasing trend, which seriously affects women's reproductive health and quality of life. At the same time, the pathogens of cervical erosion have also changed. More and more data indicate that Chlamydia trachomatis (CT), *Neisseria gonorrhoeae* (NG), Herpes simplex virus (HSV), Ureaplasma urealyticum (Uu), *Trichomonas vaginalis* (TV), and *Candida* (CA) infections are all related to cervicitis[3-5].

The main symptoms of cervical erosion are increased leucorrhea with purulent and contact bleeding, lumbosacral pain, infertility and the like. At present, there are many methods for treating cervical erosion, including oral medicine, vaginal medicine, local physiotherapy of the cervix, and surgical treatment. For patients with mild cervical erosion, regardless of the treatment, although the length of treatment is different, they all give good results. However, for the patients with severe cervical erosion, oral drug therapy have slow onset of action and low local plasma concentrations, making it difficult to achieve the desired effect, and simple vaginal drug treatment requires long course of treatment, which also has poor efficacy, unstable effects, and the high probability of recurrence. The simple vaginal drug treatment has long course of treatment, poor efficacy, unstable therapeutic effect, and high recurrence rate. Surgical treatment is costly, resulting in serious damage with long recover time, which is difficult for patients to accept.

Plasmin is a key component of the plasminogen activation system (PA system). It is a broad-spectrum protease, which can hydrolyze several components of the extracellular matrix (ECM) including fibrin, gelatin, fibronectin, laminin, and proteoglycans[6]. In addition, plasmin can activate some pro-MMPs to form active metalloproteinases (MMPs). Therefore plasmin is considered to be an important upstream regulator of extracellular proteolysis[7,8]. Plasmin is formed by proteolysis of plasminogen by two physiological PAs: tissue plasminogen activator (tPA) or urokinase plasminogen activator (uPA). Due to the relatively high level of plasminogen in plasma and other body fluids, it is traditionally believed that the regulation of the PA system is primarily achieved through PA synthesis and the activity level. The synthesis of PA system components is strictly regulated by different factors such as hormones, growth factors and cytokines. In addition, there are also specific physiological inhibitors of plasmin and PA. The major inhibitor of plasmin is α2-antiplasmin. The surface of certain cells has a uPA-specific cell surface receptor (uPAR) with direct hydrolytical activity[9,10].

Plasminogen (plg) is a single-stranded glycoprotein consisting of 791 amino acids and has a molecular weight of approximately 92 kDa[11,12]. Plasminogen is mainly synthesized in the liver and is abundantly present in the extracellular fluid. Plasminogen level in plasma is approximately 2 μM. Therefore, plasminogen is a huge potential source for proteolytic activity in tissues and body fluids[13,14]. There are two molecular forms of plasminogen: Glu-plasminogen and Lys-plasminogen. Naturally secreted and uncleaved forms of plasminogen have an amino-terminal (N-terminal) glutamic acid and are therefore referred to as glutamate-plasminogen. However, in the presence of plasmin, glutamate-plasminogen is hydrolyzed to lysine-plasminogen at Lys76-Lys77. Compared to glutamate-plasminogen, lysine-plasminogen has a higher affinity for fibrin and can be activated by PA at a higher rate. The Arg560-Val561 peptide bonds of these two forms of plasminogen can be cleaved by uPA or tPA, leading to the formation of disulfide-linked double-strand protease plasmin[15]. The amino-terminal portion of plasminogen contains five homotrimeric rings, the so-called kringle, and the carboxy-terminal portion contains a protease domain. Some kringles contain lysine binding sites that mediate the specific interaction of plasminogen with fibrin and its inhibitor alpha2-AP. Recently discovered a 38 kDa fragment of plasminogen including kringle1-4, which is a potent inhibitor of angiogenesis. This fragment is named angiostatin and can be produced by proteolysis of plasminogen by several proteases.

The main substrate of plasmin is fibrin, and the dissolution of fibrin is the key to prevent pathological thrombosis[16]. Plasmin also has substrate specificity for several components of ECM, including laminin, fibronectin, proteoglycans, and gelatin, indicating that plasmin also plays an important role in ECM remodeling[12,17,18]. Indirectly, plasmin can also degrade other components of the ECM by converting certain protease precursors into active proteases, including MMP-1, MMP-2, MMP-3, and MMP-9. Therefore, it has been suggested that plasmin is an important upstream regulator of extracellular proteolysis[19]. In addition, plasmin has the ability to activate certain potential forms of growth factors[20-22].

The present inventors have found through research that plasminogen has unexpected effects in the prevention and/or treatment of cervical erosion, which is particularly manifested in the repair of damage and inflammation. The use of plasminogen to prevent and/or treat cervical erosion has superior advantages in terms of efficacy, patient tolerance, and convenience of treatment. Therefore, fibrinogen may become a novel strategy for preventing and/or treating cervical erosion.

SUMMARY

The present invention relates to the prevention and/or treatment of cervical erosion by plasminogen. The inventors have surprisingly found that plasminogen exhibits prominent prophylactic and/or therapeutic effects in the prevention and/or treatment of cervical erosion and can effectively promote the repair of damaged tissues.

In one aspect, the present invention relates to a novel method of preventing and/or treating cervical erosion and the related disorders thereof, and use of plasminogen or plasmin for preventing and/or treating cervical erosion and the related disorders thereof. The method or use includes administering plasminogen or plasmin to a subject in vivo. The above-mentioned cervical erosion includes true erosion and pseudo-erosion. The subject is a mammal, preferably a human. In one embodiment, the cervical erosion is cervical erosion caused by any reason, specifically, cervical erosion caused by damage such as inflammation.

In one embodiment, the subject has low level of plasminogen or plasmin. Specifically, the low level is innate, secondary, and/or local.

In one embodiment, the plasminogen has at least 80%, 85%, 90%, 95%, 96%, 97%, 98% or 99% sequence identity with SEQ ID NO. 2, 6, 8, 10 or 12 and still has plasminogen activity. In one embodiment, the plasminogen has 1-100, 1-90, 1-80, 1-70, 1-60, 1- 50, 1-45, 1-40, 1-35, 1-30, 1-25, 1-20, 1-15, 1-10, 1-5, 1-4, 1-3, 1-2, 1 amino acid of addition, deletion and/or substitution on the basis of SEQ ID NO. 2, 6, 8, 10 or 12 and still has plasminogen activity. In one embodiment, the plasminogen is a protein that comprises plasminogen active fragments and still has plasminogen activity. In one embodiment, the plasminogen is selected from the group consisting of Glu-plasminogen, Lys-plasminogen, mini-plasminogen, micro-plasminogen, δ-plasminogen or any combination thereof. In another embodiment, the plasminogen is a conservative substitution variant selected from variants of Glu-plasminogen, Lys-plasminogen, mini-plasminogen, δ-plasminogen or micro-plasminogen. In one embodiment, the plasminogen is human native plasminogen, such as an ortholog of the plasminogen as shown in SEQ ID NO. 2. For example, the plasminogen can be a plasminogen ortholog of primates or rodents such as gorilla, rhesus monkey, murine, cow, horse, dog. Most preferably, the plasminogen of the present invention has the amino acid sequence shown as SEQ ID No. 2SEQ ID No. 2, 6, 8, 10, or 12.

In one embodiment, the plasminogen or plasmin is administered systemically or topically, preferably by intravenous, intramuscular, subcutaneous, local injection, rectal, vaginal administration. In one embodiment, the topical administration is performed by applying a plasminogen-containing dressing to the cervical erosion area.

In one embodiment, the plasminogen is administered in combination with a suitable polypeptide carrier or stabilizer. In one embodiment, the plasminogen is administered at a dose of 0.0001-2000 mg/kg, 0.001-800 mg/kg, 0.01-600 mg/kg, 0.1-400 mg/kg, 1-200 mg/kg, 1-100 mg/kg, 10-100 mg/kg (calculated by per kg body weight) or 0.0001-2000 mg/cm2, 0.001-800 mg/cm2, 0.01-600 mg/cm2, 0.1-400 mg/cm2, 1-200 mg/cm2, 1-100 mg/cm2, 10-100 mg/cm2 (calculated by per square centimeter body surface area) per day, preferably at least once, preferably at least administrated every day. In the case of topical administration, the above dosages may also be further adjusted based on the circumstances.

The aforementioned plasminogen or plasmin is administered alone or in combination with other drugs or therapies, including anti-bacterial drugs, anti-viral drugs, anti-fungal drugs, anti-trichombic drugs, anti-thrombotic drugs, anti-diabetic drugs, physical therapy, laser therapy, local surgical therapy, etc.

In another aspect, the present invention relates to the use of plasminogen or plasmin for the preparation of a medicament for preventing and/or treating cervical erosion in a subject. The invention also relates to a method for preparing a medicament, which comprises preparing plasminogen or plasmin and a pharmaceutically acceptable carrier into a medicament to treat the cervical erosion of a subject. In one embodiment, the cervical erosion includes true erosion and pseudo-erosion. The subject is a mammal, preferably a human. In one embodiment, the cervical erosion is cervical erosion caused by any reason, specifically, cervical erosion caused by damage such as inflammation.

In one embodiment, the subject has low level of plasminogen or plasmin. Specifically, the low level is innate, secondary, and/or local.

In one embodiment, the plasminogen has at least 80%, 85%, 90%, 95%, 96%, 97%, 98% or 99% sequence identity with SEQ ID NO. 2, 6, 8, 10 or 12 and still has plasminogen activity. In one embodiment, the plasminogen has 1-100, 1-90, 1-80, 1-70, 1-60, 1- 50, 1-45, 1-40, 1-35, 1-30, 1-25, 1-20, 1-15, 1-10, 1-5, 1-4, 1-3, 1-2, 1 amino acid of addition, deletion and/or substitution on the basis of SEQ ID NO. 2, 6, 8, 10 or 12 and still has plasminogen activity. In one embodiment, the plasminogen is a protein that comprises plasminogen active fragments and still has plasminogen activity. In one embodiment, the plasminogen is selected from the group consisting of Glu-plasminogen, Lys-plasminogen, mini-plasminogen, micro-plasminogen, δ-plasminogen or any combination thereof. In another embodiment, the plasminogen is a conservative substitution variant selected from variants of Glu-plasminogen, Lys-plasminogen, mini-plasminogen, δ-plasminogen or micro-plasminogen. In one embodiment, the plasminogen is human native plasminogen, such as an ortholog of the plasminogen as shown in SEQ ID NO. 2. For example, the plasminogen can be a plasminogen ortholog of primates or rodents such as gorilla, rhesus monkey, murine, cow, horse, dog. Most preferably, the plasminogen of the present invention has the amino acid sequence shown as SEQ ID No. 2, 6, 8, 10, or 12.

In one embodiment, the plasminogen or plasmin is administered systemically or topically, preferably by intravenous, intramuscular, subcutaneous, local injection, rectal, vaginal administration. In one embodiment, the topical administration is performed by applying a plasminogen-containing dressing to the cervical erosion area.

In one embodiment, the plasminogen is administered in combination with a suitable polypeptide carrier or stabilizer. In one embodiment, the plasminogen is administered at a dose of 0.0001-2000 mg/kg, 0.001-800 mg/kg, 0.01-600 mg/kg, 0. 1-400 mg/kg, 1-200 mg/kg, 1-100 mg/kg, 10-100 mg/kg (calculated by per kg body weight) or 0.0001-2000 mg/cm2, 0.001-800 mg/cm2, 0.01-600 mg/cm2, 0. 1-400 mg/cm2, 1-200 mg/cm2, 1-100 mg/cm2, 10-100 mg/cm2 (calculated by per square centimeter body surface area) per day, preferably at least once, preferably at least administrated every day. In the case of topical administration, the above dosages may also be further adjusted based on the circumstances.

The aforementioned plasminogen or plasmin is administered alone or in combination with other drugs or therapies, including anti-bacterial drugs, anti-viral drugs, anti-fungal drugs, anti-trichombic drugs, anti-thrombotic drugs, anti-diabetic drugs, physical therapy, laser therapy, local surgical therapy, etc.

In another aspect, the present invention relates to the plasminogen or plasmin for use in the prevention and/or treatment of cervical erosion, as well as a pharmaceutical composition comprising the plasminogen or plasmin for use in the prevention and/or treatment of cervical erosion. In one embodiment, the cervical erosion includes true erosion and pseudo-erosion. The subject is a mammal, preferably a human. In one embodiment, the cervical erosion is cervical erosion caused by any reason, specifically, cervical erosion caused by damage such as inflammation.

In one embodiment, the subject has low level of plasminogen or plasmin. Specifically, the low level is innate, secondary, and/or local.

In one embodiment, the plasminogen has at least 80%, 85%, 90%, 95%, 96%, 97%, 98% or 99% sequence identity with SEQ ID NO. 2, 6, 8, 10 or 12 and still has plasminogen activity. In one embodiment, the plasminogen has 1-100, 1-90, 1-80, 1-70, 1-60, 1- 50, 1-45, 1-40, 1-35, 1-30, 1-25, 1-20, 1-15, 1-10, 1-5, 1-4, 1-3, 1-2, 1 amino acid of addition, deletion and/or substitution on the basis of SEQ ID NO. 2, 6, 8, 10 or 12 and still has plasminogen activity. In one embodiment, the plasminogen is a protein that comprises plasminogen active fragments and still has plasminogen activity. In one embodiment, the plasminogen is selected from the group consisting of Glu-plasminogen, Lys-plasminogen, mini-plasminogen, micro-plasminogen, δ-plasminogen or any combination thereof. In another embodiment, the plasminogen is a conservative substitution variant selected from variants of Glu-plasminogen, Lys-plasminogen, mini-plasminogen, δ-plasminogen or micro-plasminogen. In one embodiment, the plasminogen is human native plasminogen, such as an ortholog of the plasminogen as shown in SEQ ID NO. 2. For example, the plasminogen can be a plasminogen ortholog of primates or rodents such as gorilla, rhesus monkey, murine, cow, horse, dog. Most preferably, the plasminogen of the present invention has the amino acid sequence shown as SEQ ID No. 2, 6, 8, 10, or 12.

In one embodiment, the plasminogen or plasmin is administered systemically or topically, preferably by intravenous, intramuscular, subcutaneous, local injection, rectal, vaginal administration. In one embodiment, the topical administration is performed by applying a plasminogen-containing dressing to the cervical erosion area.

In one embodiment, the plasminogen is administered in combination with a suitable polypeptide carrier or stabilizer. In one embodiment, the plasminogen is administered at a dose of 0.0001-2000 mg/kg, 0.001-800 mg/kg, 0.01-600 mg/kg, 0. 1-400 mg/kg, 1-200 mg/kg, 1-100 mg/kg, 10-100 mg/kg (calculated by per kg body weight) or 0.0001-2000 mg/cm2, 0.001-800 mg/cm2, 0.01-600 mg/cm2, 0. 1-400 mg/cm2, 1-200 mg/cm2, 1-100 mg/cm2, 10-100 mg/cm2 (calculated by per square centimeter body surface area) per day, preferably at least once, preferably at least administrated every day. In the case of topical administration, the above dosages may also be further adjusted based on the circumstances.

The aforementioned plasminogen or plasmin is administered alone or in combination with other drugs or therapies, including anti-bacterial drugs, anti-viral drugs, anti-fungal drugs, anti-trichombic drugs, anti-thrombotic drugs, anti-diabetic drugs, physical therapy, laser therapy, local surgical therapy, etc.

In another aspect, the present invention relates to an article of manufacture or a kit comprising plasminogen or plasmin for preventing and/or treating cervical erosion in a subject. Preferably, the article or kit further comprises a container containing one or more other drugs. The article or kit may also contain instructions indicating that the plasminogen or plasmin is used to prevent and/or treat the cervical erosion, and may further describe that the plasminogen or plasmin is administered simultaneously, before, and/or after other drugs or therapies. In one embodiment, the other drugs or therapies includes anti-bacterial drugs, anti-viral drugs, anti-fungal drugs, anti-trichombic drugs, anti-thrombotic drugs, anti-diabetic drugs, physical therapy, laser therapy, local surgical therapy, etc.

In one embodiment, the instruction may further describe that the plasminogen or plasmin can be administered systemically or topically, preferably by intravenous, intramuscular, subcutaneous, local injection, rectal, vaginal administration. In one embodiment, the topical administration is performed by applying a plasminogen-containing dressing to the cervical erosion area.

In one embodiment, the cervical erosion includes true erosion and pseudo-erosion. The subject is a mammal, preferably a human. In one embodiment, the cervical erosion is cervical erosion caused by any reason, specifically, cervical erosion caused by damage such as inflammation.

In one embodiment, the subject has low level of plasminogen or plasmin. Specifically, the low level is innate, secondary, and/or local.

In one embodiment, the plasminogen has at least 80%, 85%, 90%, 95%, 96%, 97%, 98% or 99% sequence identity with SEQ ID NO. 2, 6, 8, 10 or 12 and still has plasminogen activity. In one embodiment, the plasminogen has 1-100, 1-90, 1-80, 1-70, 1-60, 1- 50, 1-45, 1-40, 1-35, 1-30, 1-25, 1-20, 1-15, 1-10, 1-5, 1-4, 1-3, 1-2, 1 amino acid of addition, deletion and/or substitution on the basis of SEQ ID NO. 2, 6, 8, 10 or 12 and still has plasminogen activity. In one embodiment, the plasminogen is a protein that comprises plasminogen active fragments and still has plasminogen activity. In one embodiment, the plasminogen is selected from variants of Glu-plasminogen, Lys-plasminogen, mini-plasminogen, micro-plasminogen, δ-plasminogen or any combination thereof. In another embodiment, the plasminogen is a conservative substitution variant selected from variants of Glu-plasminogen, Lys-plasminogen, mini-plasminogen, δ-plasminogen or micro-plasminogen. In one embodiment, the plasminogen is human native plasminogen, such as an ortholog of the plasminogen as shown in SEQ ID NO. 2. For example, the plasminogen can be a plasminogen ortholog of primates or rodents such as gorilla, rhesus monkey, murine, cow, horse, dog. Most preferably, the plasminogen of the present invention has the amino acid sequence shown as SEQ ID No. 2, 6, 8, 10, or 12.

The present invention explicitly encompasses all the combinations of technical features belonging to the embodiments of the present invention, and these combined technical solutions have been explicitly disclosed in the present application, just as the above technical solutions have been individually and explicitly disclosed. In addition, the present invention also explicitly covers all sub-combinations of the various embodiments and elements thereof, and is disclosed herein as each such sub-combination is individually and explicitly disclosed herein.

DETAILED DESCRIPTION

1. Definition

"Cervical erosion" is the most common forms of chronic cervical inflammation, which often manifests as the epithelial surface of the cervix falls off or is replaced by another tissue of the cervix, and even visible underlying blood vessels and red tissue forming true erosion or pseudo-erosion.

"True erosion" is due to long-term stimulation of the surface secretions of the cervix and infiltration of squamous epithelium around the outside of the cervix, together with inflammatory infiltration, making the squamous epithelium covering the surface of the cervix falls off and forms an ulcer.

"Pseudo-erosion" appears like erosion because after the cervical squamous epithelium is detached, it is replaced by the hyperplasia and outward migration of columnar epithelium of cervical mucosa, and as the monolayer of columnar epithelium covered is very thin, the underlying blood vessels are clearly visible, which appears erosion-like. Pseudo-erosion is the most common clinical cervical erosion.

Cervical erosion can be divided into three types according to the surface conditions:

(1) In the early stages of inflammation, the erosion surface is covered only by monolayer of columnar epithelium with a flat surface, which is called simplex erosion;

(2) Then, due to excessive hyperplasia of the glandular epithelium together with stroma, the erosive surface is uneven and granular, which is called granular erosion;

(3) When stromal hyperplasia is significant, the surface unevenness is even more pronounced, showing a papillary shape, called papillaryerosion.

"Columnar epithelial cells" are cervical columnar epithelial cells, wherein the monolayer of columnar epithelium consists of a layer of prismatic cells. The nucleus is oval and located at the base of the cell. The monolayer of the columnar epithelium is distributed on the luminal surface of the stomach, intestine, uterus, and fallopian tube, and its function is mainly to absorb and secrete.

"Squamous epithelial cell" is one type of epithelial cell tissue. Epithelial tissue, also known as epithelium, is an important structure for lining or covering other tissues. It consists of dense epithelial cells and a small amount of intercellular substance. The structural feature is that the cells are tightly bound and there is very few intercellular substance. It usually has the functions of protection, absorption, secretion, and excretion. Epithelial tissue can be divided into three categories: covered epithelium, glandular epithelium and sensory epithelium. The covered epithelium is classified into squamous epithelium, columnar epithelium, cuboid epithelium, and transitional epithelium according to the shape of the cells in a section perpendicular to the epithelial surface.

In terms of the pathological manifestations of cervical erosion, due to the low resistance of the cervical columnar epithelium, the pathogens are easily invaded to cause inflammation. When the columnar epithelium is injured, the columnar epithelium of the cervix mucosa hyperplasia, and extends to the defect of the phosphiform epithelium in the uterine vagina and covers the wound surface, replacing the area of the original phosphorus-like epithelial defect. As the columnar epithelium is thin, the capillary blood vessels underneath the mucous membranes are clearly visible. Therefore, the mucous membranes of the outer cervix lesions are seen as bright red erosion-like areas. Therefore, internationally, cervical erosion is also referred to as "cervical epithelium ectopicity".

"Plasmin" is a very important enzyme existing in blood and can hydrolyze fibrin clots into fibrin degradation products and D-dimers.

"Plasminogen" is the zymogen form of plasmin based on the sequence in the Swiss prot and consists of 810 amino acids calculated from the natural human plasminogen amino acid sequence (SEQ ID NO:4) containing a signal peptide. It is a glycoprotein having a molecular weight of about 90 kD, which is mainly synthesized in the liver and can be circulated in the blood, and the cDNA sequence encoding the amino acid sequence is shown in SEQ ID NO:3. Full-length plasminogen contains seven domains: a serine protease domain at the C-terminus, a Pan Apple (PAp) domain at the N-terminus, and five Kringle domains (Kringle 1-5). Referring to the sequence in swiss prot, its signal peptide includes residues Met1-Gly19, PAp includes residues Glu20-Val98, Kringle1 includes residues Cys103-Cys181, Kringle2 includes residues Glu184-Cys262, Kringle3 includes residues Cys275-Cys352, Kringle4 includes residues Cys377-Cys454, and Kringle5 includes residues Cys481-Cys560. According to NCBI data, the serine protease domain includes residues Val581-Arg804.

Glu-plasminogen is a natural full-length plasminogen and consists of 791 amino acids (having no signal peptide of 19 amino acids). The cDNA sequence encoding this sequence is shown in SEQ ID NO:1, and its amino acid sequence is as shown in SEQ ID NO. 2. In vivo, Lys-plasminogen, which is formed by hydrolysis of amino acids 76-77 of Glu-plasminogen, is also present, as shown in SEQ ID NO: 6. The cDNA sequence encoding this amino acid sequence is as shown in SEQ ID NO. 5. Delta-plasminogen is a fragment of full-length plasminogen, which lacks the Kringle2-Kringle5 structure and contains only Kringle1 and serine protease domains[23,24]. δ-plasminogen has been reported in the literature. There is literature reporting the amino acid sequence of δ-plasminogen (SEQ ID NO: 8)[24], and the cDNA sequence encoding this amino acid sequence is as shown in SEQ ID NO: 7. Mini-plasminogen consists of Kringle5 and serine protease domains, and it has been reported to include residues Val443-Asn791 (starting from the Glu residue of the Glu-plasminogen sequence which does not contain a signal peptide)[25]. The amino acid sequence is shown in SEQ ID NO: 10, and the cDNA sequence encoding the amino acid sequence is shown in SEQ ID NO:9. The micro-plasminogen contains only the serine protease domain, and its amino acid sequence has been reported to include the residue Ala543-Asn791 (starting from the Glu residue of the Glu-plasminogen sequence which does not contain a signal peptide)[26]. Also, the patent document CN102154253A reports that its sequence includes the residues Lys531-Asn791 (starting from the Glu residue of the Glu-plasminogen sequence which does not contain a signal peptide). The present invention refers to the sequence in the patent document CN102154253A and its amino acid sequence is shown in SEQ ID NO: 12. The cDNA sequence encoding this amino acid sequence is shown in SEQ ID NO:11.

In the present invention, "plasmin" is used interchangeably with "fibrinolysin" and "fibrinoclase", and the terms have the same meaning; and "plasminogen" is used interchangeably with "fibrinolytic zymogen" and "fibrinoclase zymogen", and the terms have the same meaning.

Those skilled in the art can understand that all the technical solutions of the plasminogen of the present invention are suitable for plasmin. Therefore, the technical solutions described in the present invention cover plasminogen and plasmin.

Those skilled in the art can understand that the present invention can prevent the occurrence of other diseases caused by cervical erosion such as cervical cancer, cervicitis, salpingitis, adnexitis, pelvic inflammatory disease and the like by preventing and/or treating cervical erosion. Therefore, the prevention of these diseases is also covered by the present invention.

In the course of circulation, plasminogen adopts a closed, inactive conformation. However, when bound to the thrombus or cell surface, it is mediated by plasminogen activator (PA), which is converted into active plasmin in an open conformation. The active plasmin can further hydrolyze the fibrin clot to fibrin degradation products and D-dimer, which in turn dissolves the thrombus. The active plasmin can further hydrolyze the fibrin clot to fibrin degradation products and D-dimer, which in turn dissolves the thrombus. The PAp domain of plasminogen contains an important cluster that maintains plasminogen in an inactive closed conformation, whereas the KR domain is capable of binding to lysine residues present in the receptors and substrates. A variety of enzymes acting as plasminogen activators are known including: tissue plasminogen activator (tPA), urokinase plasminogen activator (uPA), kallikrein, and coagulation factor XII (Hagman factor) etc.

"Plasminogen active fragment" refers to an active fragment of the plasminogen that binds to the target sequence in a substrate and exerts a proteolytic function. The technical solution involving plasminogen in the present invention encompasses a technical solution of replacing plasminogen with a plasminogen active fragment. The plasminogen active fragment of the present invention is a protein comprising a serine protease domain of the plasminogen. Preferably, the plasminogen active fragment of the present invention comprises SEQ ID NO 14 or an amino acid sequence having at least 80%, 90%, 95%, 96%, 97%, 98%, 99% sequence homology with SEQ ID NO 14. Thus, the plasminogen of the present invention includes a protein comprising the plasminogen active fragment and still retaining the plasminogen activity.

Currently, assays for determining plasminogen and its activity in blood include: detection of tissue plasminogen activator activity (t-PAA) and detection of plasma plasminogen activator antigen (t-PAAg), detection of plasma plasminogen activity (plgA), detection of plasma plasminogen antigen (plgAg), detection of the activity of plasma plasminogen activator inhibitor, detection of plasma plasminogen activator inhibitor antigens, and plasma plasmin-antiplasmin complex assay (PAP). The most commonly used detection method is the chromogenic substrate method: streptokinase (SK) and chromogenic substrate are added to the test plasma, the PLG in the tested plasma is converted to PLM under the action of SK, and the latter acts on the chromogenic substrate which is then measured with a spectrophotometer, and the absorbance increase is proportional to the plasminogen activity. In addition, plasminogen activity in blood can also be measured by immunochemical methods, gel electrophoresis, immunonephelometry, radioimmuno-diffusion, and the like.

"Orthologues or orthologs" refer to homologs between different species, including both protein homologs and DNA homologs, and are also known as orthologous homologs and vertical homologs. The term specifically refers to proteins or genes that have evolved from the same ancestral gene in different species. The plasminogen of the present invention includes human natural plasminogen, and also includes orthologues or orthologs of plasminogens derived from different species and having plasminogen activity.

A "conservative substitution variant" refers to a change in a given amino acid residue without altering the overall conformation and function of the protein or enzyme, including but not limited to substitution of amino acids in the sequence of the parental protein with amino acids of similar properties (such as acidity, alkalinity, hydrophobicity, etc.). Amino acids with similar properties are well known. For example, arginine, histidine and lysine are hydrophilic basic amino acids and are interchangeable. Similarly, isoleucine is a hydrophobic amino acid that can be replaced by leucine, methionine or valine. Therefore, the similarity of two proteins or amino acid sequences of similar functions is different, for example, 70% to 99% similarity (identity) based on the MEGALIGN algorithm. A "conservative substitution variant" also includes a polypeptide or enzyme having 60% or more amino acid identity determined by the BLAST or FASTA algorithm, and 75% or more is preferred, 85% or more is more preferred, and even 90% or more is the most preferred. Compared to the native or parental proteins or enzymes, it possesses the same or substantially similar properties or functions.

"Isolated" plasminogen refers to plasminogen protein isolated and/or recovered from its natural environment. In some embodiments, the plasminogen will be purified to (1) have greater than 90%, greater than 95%, or greater than 98% purity (by weight), as determined by the Lowry method, eg., greater than 99% (by weight), (2) a degree sufficient to obtain at least 15 residues of the N-terminal or internal amino acid sequence using a rotating cup sequencer, or (3) homogeneity determined by SDS-PAGE using Coomassie blue or silver stained under reducing or non-reducing conditions. Isolated plasminogen also includes plasminogen prepared from recombinant cells by bioengineering techniques and isolated by at least one purification step.

The terms "polypeptide", "peptide" and "protein" are used interchangeably herein and refer to polymeric forms of amino acids of any length, which may include genetically encoded and non-genetically encoded amino acids, chemically or biochemically modified or derivatized amino acids, and polypeptides having modified peptide backbones. The term includes fusion proteins including, but not limited to, fusion proteins having heterologous amino acid sequences, fusions having heterologous and homologous leader sequences (with or without N-terminal methionine residues), and the like.

"The percentage of amino acid sequence identity (%)" with respect to the reference polypeptide sequence is defined as the percentage of amino acid residues in the candidate sequence that are identical to those in the reference polypeptide sequence when a gap is introduced as necessary to achieve maximal percent sequence identity and no conservative substitutions are considered as part of sequence identity. The comparison for purposes of determining percent amino acid sequence identity can be achieved in a variety of ways within the skill in the art, for example using publicly available computer software such as BLAST, BLAST-2, ALIGN or Megalign (DNASTAR). Those skilled in the art can determine appropriate parameters for aligning sequences, including any algorithms needed to achieve maximum contrast over the full length of the sequences being compared. However, for purposes of the present invention, the percentage of amino acid sequence identity was generated using the sequence comparison computer program ALIGN-2. In the case of comparing amino acid sequences using ALIGN-2, the % amino acid sequence identity of a given amino acid sequence A relative to a given amino acid sequence B (alternatively, it can be expressed as a given amino acid sequence A having or containing a certain % amino acid sequence identity with respect to, with, or for a given amino acid sequence B) can be calculated as:

Percentage $X/Y*100$

Wherein X is the number of identically matched amino acid residues scored by the sequence alignment program ALIGN-2 in the alignments between A and B, and Y is the total number of amino acid residues in B. It will be appreciated that when the length of amino acid sequence A is not equal to the length of amino acid sequence B, the % amino acid sequence identity of A relative to B will not equal to the % amino acid sequence identity of B relative to A. Unless specifically stated otherwise, all % amino acid sequence identity values used herein are obtained using the ALIGN-2 computer program as described in the previous paragraph.

As used herein, the terms "treating", "treatment" and "eliminating" refer to obtaining a desired pharmacological and/or physiologic effect. The effect is complete or partial prevention of the disease or its symptoms, and/or partial or complete cure of the disease and/or its symptoms, and includes: (a) preventing the occurrence of a disease in the subject, wherein the subject may have the cause of the disease, but not yet diagnosed as having the disease; (b) inhibiting the disease, i.e., arresting its onset; and (c) alleviating the disease and/or its symptoms, i.e., causing the disease and/or its symptoms to disappear.

The terms "individual", "subject" and "patient" are used interchangeably herein and refer to mammals, including but not limited to murine (rats, mice), non-human primates, humans, dogs, cats, hoofed animals (such as horses, cows, goat, pigs, goats) and the like.

A "therapeutically effective amount" or "effective amount" refers to an amount of plasminogen sufficient to effect the prevention and/or treatment of a disease when administered to a mammal or other subject to treat the disease. The "therapeutically effective amount" will vary depending on the plasminogen used, the condition of the subject to be treated, and/or the severity of the symptoms, as well as age, body weight, and the like.

2. Preparation of Plasminogen of the Present Invention

Plasminogen can be isolated from nature and purified for further therapeutic uses, and can also be synthesized by standard chemical peptide synthesis techniques. When chemically synthesized, they can be obtained via the liquid or solid phase. Solid phase polypeptide synthesis (SPPS), in which the C-terminal amino acid of the sequence is attached to an insoluble support, followed by sequential addition of the remaining amino acids in the sequence, is a method suitable for chemical synthesis of plasminogen. Various forms of SPPS, such as Fmoc and Boc, can be used to synthesize plasminogen. Techniques for solid-phase synthesis are described in Barany and Solid-Phase Peptide Synthesis; pages 3-284 in The Peptides: Analysis, Synthesis, Biology. Vol. 2: Special Methods in Peptide Synthesis, Part A., Merrifield, et al. Am. Chem. Soc., 85: 2149-2156 (1963); Stewart et al., Solid Phase Peptide Synthesis, 2nd ed. Pierce Chem. Co., Rockford, Ill. (1984); and Ganesan A. 2006 Mini Rev. Med Chem. 6:3-10 and Camarero J A et al. 2005 Protein Pept Lett. 12:723-8. Briefly, small insoluble porous beads are treated with a functional unit on which a peptide chain is constructed. After repeated cycles of coupling/deprotection, the free N-terminal amine of attached solid phase is coupled to a single N-protected amino acid unit. This unit is then deprotected to expose new N-terminal amines that can be attached to other amino acids. The peptide remains immobilized on the solid phase before it is cut off.

Standard recombinant methods can be used to produce the plasminogen of the invention. For example, nucleic acid encoding plasminogen is inserted into an expression vector so that it is operably linked to a regulatory sequence in the expression vector. The expression regulatory sequences include, but are not limited to, promoters (eg, naturally associated or heterologous promoters), signal sequences, enhancer elements, and transcription termination sequences. Regulation of the expression can be in a eukaryotic promoter system in a vector that is capable of transforming or transfecting eukaryotic host cells (eg, COS or CHO cells). Once the vector is incorporated into a suitable host, the host is maintained under conditions suitable for high-level expression of the nucleotide sequence and recovery and purification of plasminogen.

Suitable expression vectors are usually replicated in the host organism as episomes or as an integral part of the host chromosomal DNA. Typically, the expression vector contains a selection marker (e.g., ampicillin resistance, hygromycin resistance, tetracycline resistance, kanamycin resistance, or neomycin resistance) to facilitate the determination of the exogenous transformation of the desired DNA sequence to those cells.

*Escherichia coli* is an example of prokaryotic host cell that can be used to clone the subject protein-encoding polynucleotide. Other microbial hosts suitable for use include bacilli, such as *Bacillus subtilis* and other Enterobacteriaceae, such as *Salmonella, Serratia,* and various *Pseudomonas* species. In these prokaryotic hosts, expression vectors, which typically contain expression regulatory sequences (eg, origins of replication) that are compatible with the host cell, can also be generated. In addition, many promoters are well-known, such as the lactose promoter system, the tryptophan (trp) promoter system, the beta-lactamase promoter system, or the promoter system from phage lambda. The promoter usually controls expression, and optionally in the case of manipulation of gene sequences, has ribosome binding site sequences and the like to initiate and complete transcription and translation.

Other microorganisms, such as yeast, can also be used for expression. Yeast (eg, *S. cerevisiae* and *Pichia*) is an example of suitable host cells in which appropriate vectors may have expression control sequences (eg, promoters), origins of replication, termination sequences, and the like, as desired. Typical promoters include 3-phosphoglycerate kinase and other saccharolytic enzymes. Inducible yeast promoters include, in particular, promoters derived from alcohol dehydrogenase, isocytochrome C, and enzymes responsible for maltose and galactose utilization.

In addition to microorganisms, mammalian cells (eg, mammalian cells cultured in in vitro cell culture) can also be used to express and produce the protein of the invention (eg, polynucleotides encoding the subject protein). See Winnacker, From Genes to Clones, VCH Publishers, N.Y., N.Y. (1987). Suitable mammalian host cells include CHO cell line, various Cos cell lines, HeLa cells, myeloma cell lines, and transformed B cells or hybridomas. Expression vectors for these cells may contain expression control sequences, such as origins of replication, promoters and enhancers (Queen et al., Immunol. Rev. 89:49 (1986)), and necessary information processing sites, such as ribosome binding sites, RNA splice sites, polyadenylation sites, and transcription terminator sequences. Examples of suitable expression control sequences are promoters derived from white immunoglobulin genes, SV40, adenovirus, bovine papilloma virus, cytomegalovirus, and the like. See Co et al., J. Immunol. 148: 1149 (1992).

Once synthesized (chemically or recombinantly), the plasminogen of the invention can be purified according to standard procedures in the art, including ammonium sulfate precipitation, affinity columns, column chromatography, HPLC, gel electrophoresis, and the like. The plasminogen is substantially pure, e.g., at least about 80% to 85% pure, at least about 85% to 90% pure, at least about 90% to 95% pure, or 98% to 99% pure, or even more pure, for example, free of contaminants such as cell debris, macromolecules other than the subject antibody, and the like.

3. Pharmaceutical Formulations

Pharmaceutical formulations can be prepared by mixing plasminogen of desired purity with an optional pharmaceutical carrier, excipient, or stabilizer (Remington's Pharmaceutical Sciences, 16th Edition, Osol, A. ed. (1980))to form a lyophilized formulation or aqueous solution. Acceptable carriers, excipients, stabilizers are non-toxic to the recipient at the dosages and concentrations employed, and include buffers such as phosphates, citrates and other organic acids; antioxidants including ascorbic acid and methionine; preservatives (such as octadecyl dimethyl benzyl ammonium chloride; hexamethonium chloride; benzalkonium chloride; benzoxonium chloride; phenol, butanol or benzyl alcohol; alkyl p-hydroxybenzoates such as methyl or propyl p-hydroxybenzoate; catechol; resorcinol; cyclohexanol; 3-pentanol; m-cresol); low molecular weight polypeptides (less than about 10 residues); proteins such as serum albumin, gelatin or immunoglobulins; hydrophilic polymers such as polyvinylpyrrolidone; amino acids such as glycine, glutamine, asparagine, histidine, arginine or lysine; monosaccharides, disaccharides and other carbohydrates including glucose, mannose, or dextrin; chelating agents such as EDTA; sugars such as sucrose, mannitol, fucose, or sorbitol; ions such as sodium; metal complexes (eg zinc-protein complexes); and/ or non-ionic surfactants such as TWEEN™, PLURONICS™ or polyethylene glycol (PEG).

Formulations of the invention may also contain more than one active compound as desired for the particular condition being treated, preferably those that are complementary in activity and have no side effects with each other, for example, anti-infective drugs and the like.

The plasminogen of the present invention is encapsulated in microcapsules prepared by techniques such as coacervation or interfacial polymerization, for example, is incorporated in a colloidal drug delivery system (eg, liposomes, albumin microspheres, microemulsions, nanoparticles and nanocapsules) or incorporated in hydroxymethyl cellulose in a crude emulsion or gel-microcapsules and poly-(methyl methacrylate) microcapsules. These techniques are disclosed in Remington's Pharmaceutical Sciences 16th edition, Osol, A. Ed. (1980).

The plasminogen of the present invention for in vivo administration must be sterile. This can be easily achieved by filtration through a sterile filter before or after lyophilization and reconstitution.

The plasminogen of the present invention can be prepared into sustained-release preparations. Suitable examples of sustained-release preparations include solid hydrophobic polymer semi-permeable matrices having a certain shape and containing glycoproteins, such as films or microcapsules. Examples of sustained-release matrices include polyesters, hydrogels (such as poly(2-hydroxyethyl-methacrylate) (Langer et al., J. Biomed. Mater. Res., 15: 167-277 (1981); Langer, Chem. Tech., 12:98-105 (1982)) or poly (vinyl alcohol), polylactide (U.S. Pat. No. 3,773,919, EP 58,481), L-glutamic acid, and ethyl-L-glutamic acid copolymers (Sidman, et al., Biopolymers 22:547 (1983)), non-degradable ethylene-vinyl acetate(Langer, et al., supra), or degradable lactic acid-glycolic acid copolymers such as Lupron Depot™ (injectable microspheres composed of lactic acid-glycolic acid copolymer and leuprolide acetate), and poly D-(−)-3-hydroxybutyric acid. Polymers such as ethylene vinyl acetate and lactic acid-glycolic acid are able to release molecules for more than 100 days, while some hydrogels release proteins for a shorter period of time. A rational strategy for protein stabilization can be designed based on relevant mechanisms. For example, if the mechanism of agglomeration is found to be the formation of intermolecular SS bonds through thiodisulfide interchange, then it can be modified by thiol residues, lyophilization from acidic solutions, controlling humidity, using suitable additives, and developing specific polymer matrix compositions to achieve stability.

4. Administration and Dosage

The invention can be implemented in different ways, for example by intravenous, intraperitoneal, subcutaneous, intracranial, intrathecal, intraarterial (for example via carotid), intramuscular, intranasal, topical or intradermal administration or spinal cord or brain delivery to achieve the administration of the pharmaceutical composition of the present invention. Aerosol formulations, such as nasal spray formulations, include purified aqueous or other solutions of the active agent along with preservatives and isotonic agents. Such formulations are adjusted to a pH and isotonic state compatible with the nasal mucosa.

In some cases, the plasminogen pharmaceutical compositions of the present invention is modified or formulated in the following manner to provide their ability to cross the blood-brain barrier. Compositions of such plasminogen can be administered to individuals suffering from thrombotic and/or thrombotic-related diseases via a variety of enteral and parenteral routes including oral, intravenous administration, and the like.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, or fixed oils. Intravenous vehicles include liquid and nutrient supplements, electrolyte supplements, and the like. Preservatives and other additives, such as, for example, antimicrobial agents, antioxidants, chelating agents, and inert gases, may also be present.

The physicians will determine the dosage regimen based on various clinical factors. As is well known in the arts, the dose for a patient depends on a variety of factors including the size, body surface area, age, the specific compound to be administered, sex, frequency and route of administration, overall health, and other drugs administered simultaneously. The dose of the pharmaceutical composition containing plasminogen of the present invention is, for example, about 0.0001 to 2000 mg/kg, or about 0.001 to 500 mg/kg (eg 0.02 mg/kg, 0.25 mg/kg, 0.5 mg/kg, 0.75 mg/kg, 10 mg/kg, 50 mg/kg, etc. )of the subject's body weight. For example, the dose is 1 mg/kg body weight or 50 mg/kg body weight or in the range of 1-50 mg/kg, or at least 1 mg/kg. Dosages above or below this exemplary range are also contemplated, especially considering the above factors. The intermediate dose in the above range is also included in the scope of the present invention. Subjects may be administered such doses daily, on alternate days, weekly or on any other schedule determined by empirical analysis. Exemplary dosage schedules include 1-10 mg/kg for consecutive days. In the administration process of the present invention, real-time evaluation and regular assessment of the therapeutic effect and safety of thrombosis and thrombosis-related diseases are required.

5. Evaluation for the Effect of Cervical Erosion Treatment (1) Gynecological examination, wherein the size, shape, texture, thickness of the cervix, and whether there is contact bleeding are examined.

(2) Cervical smears. Cytology is a routine examination for gynecology. It is simple, easy, and cost-effective. It is the most important auxiliary screening method and the primary screening method for cancer screening and prevention.

Cervical smears, is a mean to take a small sample of cells from the cervix portion, on glass, and then examine the abnormality under a microscope.

(3) Colposcopy, which can quickly find invisible lesions. Taking a suspicious site biopsy to colposcopy can significantly improve the accuracy of biopsy.

(4) TCT examination, which is an abbreviation for liquid-based thin-layer cell detection.

In TCT, liquid-based thin-layer cell detection system is used to detect cervical cells and perform cytological classification diagnosis. It is currently the most advanced cervical cancer technology in the world. Compared with the traditional cervical smear, it significantly improves the satisfaction of the specimen and the abnormal cell detection rate of the cervix.

(5) Cervical biopsy. The pathological examination of cervical biopsy is the basis for the diagnosis of cervical cancer. A cervical biopsy is a biopsy of the cervix, which takes a small piece or pieces of tissue from the cervix for pathological examination to confirm the diagnosis.

6. Article of Manufacture or Kit

One embodiment of the invention relates to an article of manufacture or a kit comprising the plasminogen or plasmin of the invention. The article of manufacture preferably includes a container, label or package insert. Suitable containers include bottles, vials, syringes, and the like. The container can be made of various materials such as glass or plastic. The container contains a composition that is effective to treat the disease or condition of the present invention and has a sterile access (for example, the container may be an intravenous solution bag or vial containing a stopper that can be pierced by a hypodermic injection needle). At least one active agent in the composition is plasminogen or plasmin. The container or the attached label indicates that the composition is used to treat the cervical erosion of the present invention. The article may further comprise a second container containing a pharmaceutically acceptable buffer, such as phosphate buffered saline, Ringer's solution, and dextrose solution. It may further contain other substances required from a commercial and user perspective, including other buffers, diluents, filters, needles and syringes. In addition, the article includes a package insert with instructions for use, for example, indicating the user to administrate the composition of plasminogen as well as other accompanied drugs to the patient.

EXAMPLES

Figure 1:
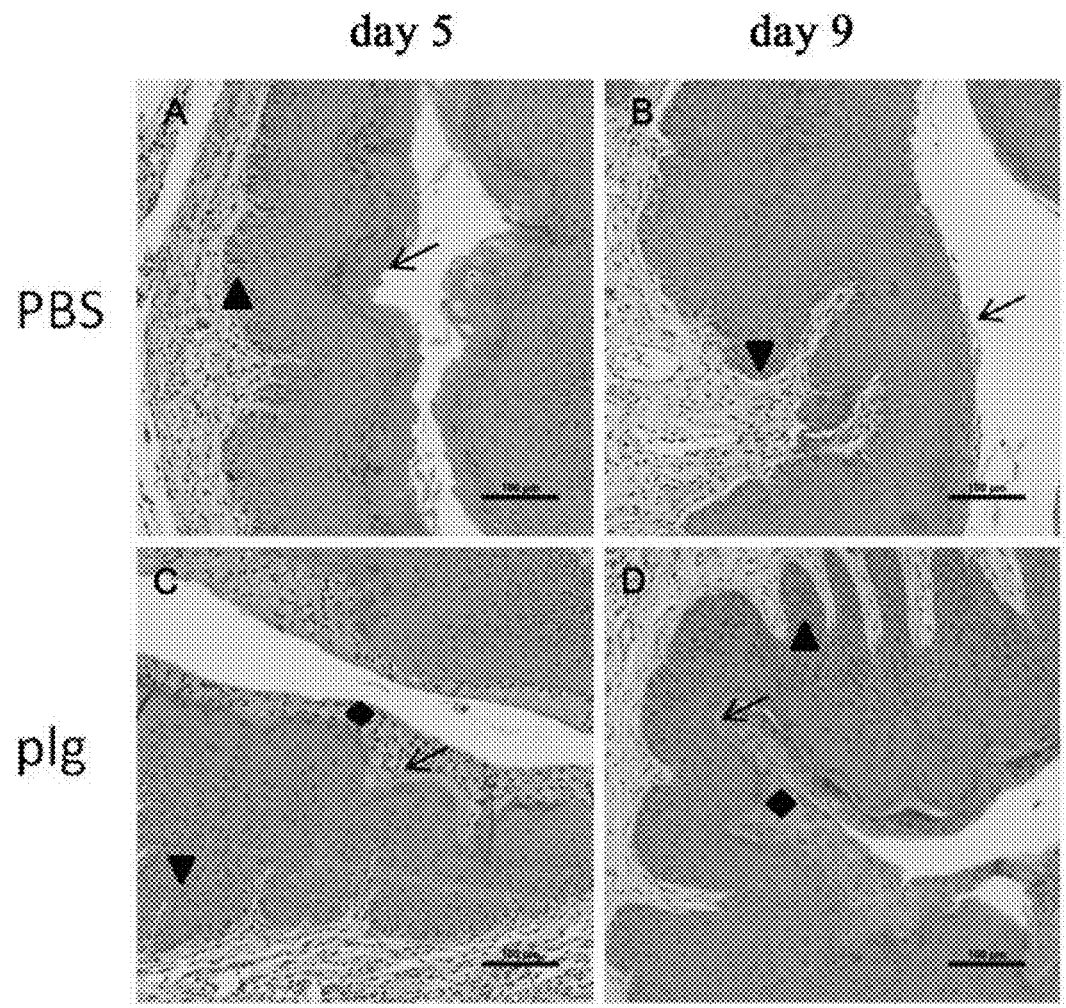
FIG. 1 shows the results of cervical HE staining on day 5 and day 9 after the administration of plasminogen or PBS to plg+/+ cervical erosion mouse model.

Example 1 Protective Effect of Plasminogen on plg+/+ Cervical Erosion Mouse Model In this experiment, 12 healthy female plg+/+ mice aged 6-7 weeks were randomly divided into two groups, 6 mice in each group, which were given vehicle PBS control and plasminogen, respectively. One day before modeling, mice were weighed and grouped. Then the model of cervical erosion was established. The cervix of the mouse was injected with 0.01 mL of phenol paste per day for 4 continuous treatments. Formulation scheme of phenolic paste: phenol was melted at 60° C., then 4 g Arabic gum powder and 5 mL distilled water were added to 3 mL of the phenol to stir and mix to obtain a milky viscous phenol paste[27]. After the model was established, plasminogen was administered to the plasminogen group at a dose of 1 mg/0.1 mL/mouse/day via tail vein injection, and the vehicle PBS control group was given the same volume of PBS. The day after modeling was day 0. On day 1, plasminogen or vehicle PBS was administered, and the administration period was 8 days. On day 5, day 9, 3mice in both groups were randomly chosen, and the mice were sacrificed by taking blood from the eyeball, and the cervical tissue was fixed in 4% paraformaldehyde for 24-48 hours. After fixation, the cervical tissue was dehydrated with alcohol gradient and permeabilized by xylene and then embedded in paraffin. The thickness of the tissue section was 5 μm. The sections were dewaxed and rehydrated, stained with hematoxylin and eosin (HE staining), differentiated with 1% hydrochloric acid, returned to blue with ammonia, and dehydrated with ethyl alcohol and then sealed. The sections were observed under a microscope at 200 times.

HE staining results showed that on day 5, in control mice administered vehicle PBS, hyperkeratosis and shredding were observed for the mucosal stratum corneum(↓). Mild hyperplasia occurred in squamous epithelium (Δ). On day 9, the keratinized stratum corneum was basically fallen off. The surface was not smooth (↓) without epithelial repair. The squamous epithelial hyperplasia was severe (FIG. 1A, B). In the plasminogen group, some of the stratum corneum fell off on the 5th day, and the damaged epithelial surface was covered with neonatal epithelium. In the plasminogen group, on day 5, some of the stratum corneum fell off and disappeared (↓), and the damaged epithelial surface was covered with neonatal epithelium(♦). On day 9, the neonatal epithelium was further repaired and squamous metaplasia occurred(↓), covering the damaged mucosal surface (FIG. 1C, D). It can be found that the mice in the PBS control group showed severe cervical injury, and the plasminogen group showed repair. Over time, the damaged mucosal surface continued to improve, indicating that plasminogen has protective effects on cervical erosion tissues.

Example 2 Plasminogen Promotes the Repair of Cervical Injury in plg−/− Cervical Erosion Mouse Model In this experiment, 18 healthy female plg$^{-/-}$ mice aged 6-7 weeks were randomly divided into two groups, 9 mice in each group, which were given vehicle PBS control and plasminogen, respectively. One day before modeling, mice were weighed and grouped. Then the model of cervical erosion was established. The cervix of the mouse was injected with 0.01 mL of phenol paste per day for 4 continuous treatments. Formulation scheme of phenolic paste: phenol was melted at 60° C., then 4 g Arabic gum powder and 5 mL distilled water were added to 3 mL of the phenol to stir and mix to obtain a milky viscous phenol paste[27]. After the model was established, plasminogen was administered to the plasminogen group at a dose of 1 mg/0.1 mL/mouse/day via tail vein injection, and the vehicle PBS control group was given the same volume of PBS. The day after modeling was day 0. On day 1, plasminogen or vehicle PBS was administered, and the administration period was 12 days. On day 5, day 9 and day 13, 3mice in both groups were randomly chosen, and the mice were sacrificed by taking blood from the eyeball, and the cervical tissue was fixed in 4% paraformaldehyde for 24-48 hours. After fixation, the cervical tissue was dehydrated with alcohol gradient and permeabilized by xylene and then embedded in paraffin. The thickness of the tissue section was 5 μm. The sections were dewaxed and rehydrated, stained with hematoxylin and eosin (HE staining), differentiated with 1% hydrochloric acid and alcohol, returned to blue with ammonia, and dehydrated with ethyl alcohol and then sealed. The sections were observed under a microscope at 200 times.

Figure 2:
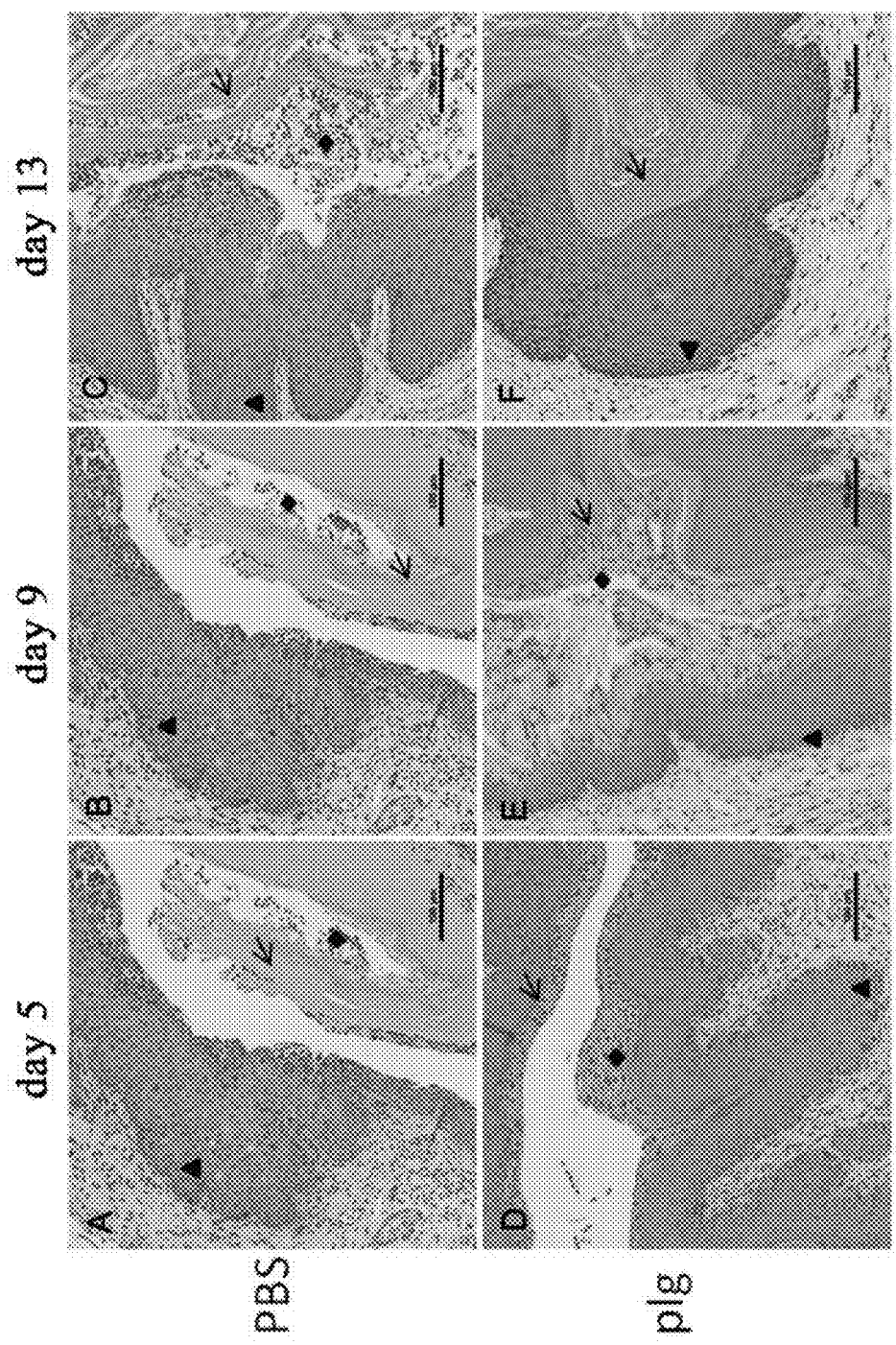
FIG. 2 shows the results of cervical HE staining on day 5, day 9 and day 13 after the administration of plasminogen or PBS to plg−/− cervical erosion mouse model.

HE staining results showed that on day 5, 9 and 13, in control mice administered vehicle PBS, the squamous epithelial stratum corneum fell off, erosion formed on the surface, keratin layer was seen in the cavity(↓), and a large number of inflammatory cells infiltrated (♦). Over time, inflammation continued to increase, and ulcers on the mucosal surface continued to increase (FIG. 2A-C). In the plasminogen group (FIG. 2D-F), on day 5, neoplastic epithelial repair occurred on the surface (↓), although degeneration and necrosis of the mucous membranes formed. On day 9, there was only a small amount of inflammatory cell infiltration in the uterine cavity, and neonatal epithelium further proliferated, and squamous epithelial stratum corneum appeared under the neonatal epithelium (↓). On day 13, there was no foreign matter in the uterine cavity, the ulcer had healed, and the surface of the squamous epithelium had been covered by the repaired stratum corneum. On day 13, there was no foreign matter in the uterine cavity, the ulcer healed and the surface of the squamous epithelium was covered by the repaired stratum corneum. plg −/− mice lack plasminogen, therefore, plasminogen was still lacking in mice given PBS vehicle, but plasminogen was replenished to mice in the plasminogen group. The vehicle PBS control group was severely damaged, and no repair was observed as the time progressed. In the plasminogen group, the cervical injury was less, and the injury was gradually repaired with the extension of the administration time. This means that plasminogen can significantly promote the repair of cervical injury in plg−/− cervical erosion mouse model.

Example 3 Plasminogen Promotes Degradation of Cervical Fibrin in plg+/+ Cervical Erosion Mouse Model In this experiment, 12 healthy female plg+/+ mice aged 6-7 weeks were randomly divided into two groups, 6 mice in each group, which were given vehicle PBS control and plasminogen, respectively. One day before modeling, mice were weighed and grouped. Then the model of cervical erosion was established. The cervix of the mouse was injected with 0.01 mL of phenol paste per day for 4 continuous treatments. Formulation scheme of phenolic paste: phenol was melted at 60° C., then 4 g Arabic gum powder and 5 mL distilled water were added to 3 mL of the phenol to stir and mix to obtain a milky viscous phenol paste[27]. After the model was established, plasminogen was administered to the plasminogen group at a dose of 1 mg/0.1 mL/mouse/day via tail vein injection, and the vehicle PBS control group was given the same volume of PBS. The day after modeling was day 0. On day 1, plasminogen or vehicle PBS was administered, and the administration period was 8 days. On day 5, day 9, 3 mice in both groups were randomly chosen, and the mice were sacrificed by taking blood from the eyeball, and the cervical tissue was fixed in 4% paraformaldehyde for 24-48 hours. After fixation, the cervical tissue was dehydrated with alcohol gradient and permeabilized by xylene and then embedded in paraffin. The thickness of the tissue section was 5 μm. The sections were dewaxed and rehydrated, and washed once, then repaired by citric acid for 30 minutes and cooled at room temperature for 10 minutes followed by gently rinse with water. Then the section was incubated with 3% hydrogen peroxide for 15 minutes and the tissue was circled by a PAP pen. The tissue was blocked in 10% normal goat serum (Vector laboratories, Inc., USA) for 1 hour; then the goat serum was discarded. Then it was incubated overnight at 4° C. in rabbit anti-mouse fibrin (fibrinogen) antibody (Abcam) and washed twice in TBS for 5 minutes each. Then it was incubated for 1 hour at room temperature with goat anti-rabbit IgG (HRP) (Abcam) secondary antibody and washed twice in TBS for 5 minutes each. The color was developed with a DAB kit (Vector laboratories, Inc., USA). After washing with water for 3 times, it was hematoxylin counterstained for 30 seconds and washed with running water for 5 minutes. The slices were gradiently dehydrated and permeabilized and observed under a microscope at 200 times.

Fibrinogen is a precursor of fibrin. In the presence of tissue damage, fibrinogen is hydrolyzed into fibrin as a stress response to the damage[28-30]. Therefore, fibrin levels can be used as a sign of the degree of damage.

Figure 3:
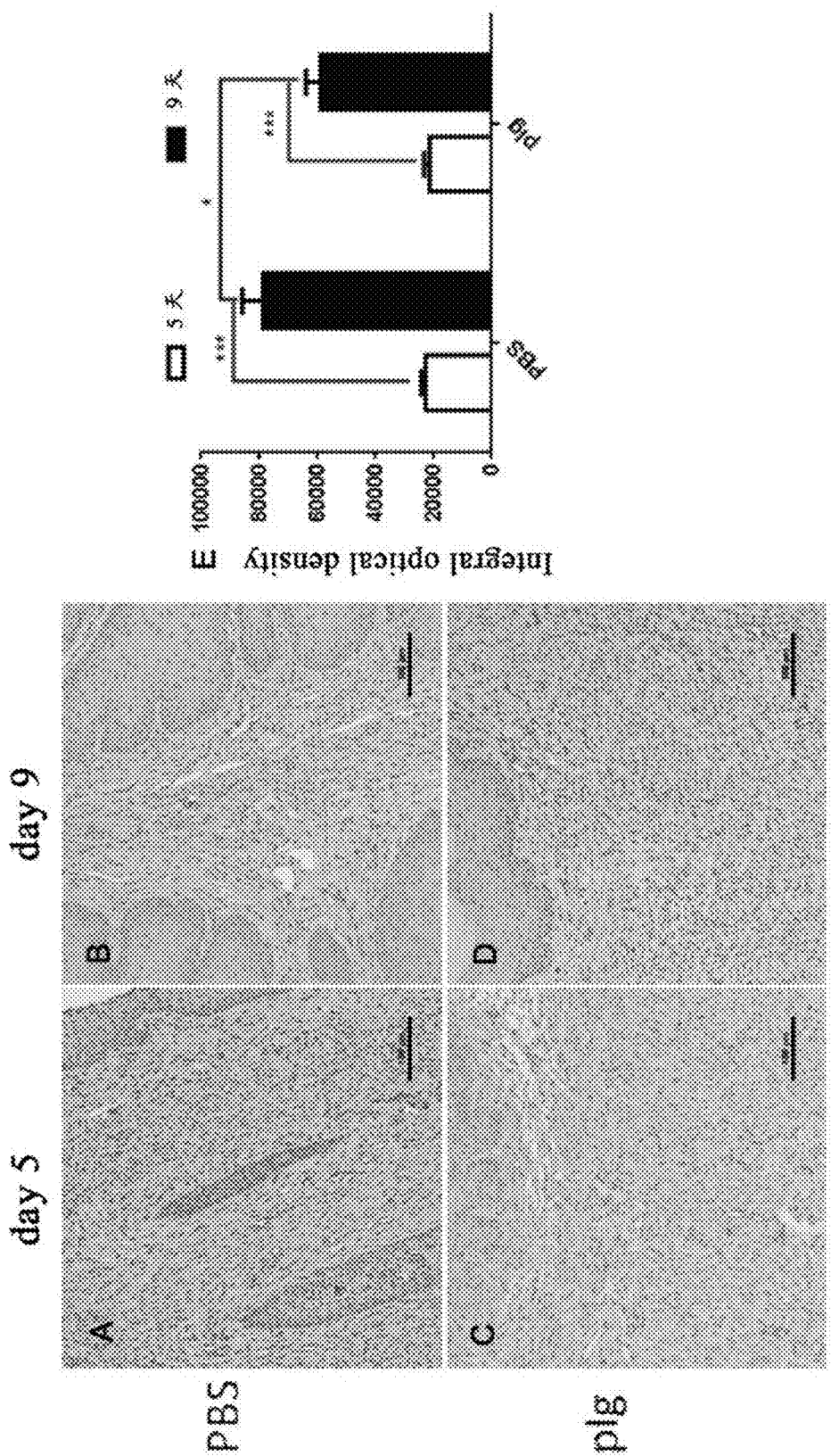
FIG. 3 shows the results by observing cervical fibrin immunostaining on day 5 and day 9 after the administration of plasminogen or PBS to plg+/+ cervical erosion mouse model.

The results showed that the positive staining of cervical fibrin in the PBS control group (FIG. 3A, B) and the plasminogen group (FIG. 3C, D) on day 9 was deeper than that of day 5. However, the positive staining of the PBS control group was deeper than that of the plasminogen group, and the difference was statistically significant (FIG. 3E). This shows that plasminogen can reduce the deposition of fibrin, and reduced cervix damage in plg+/+ cervical erosion mouse model.

Example 4 Plasminogen Promotes Degradation of Cervical Fibrin in plg-/- Cervical Erosion Mouse Model In this experiment, 18 healthy female plg$^{-/-}$ mice aged 6-7 weeks were randomly divided into two groups, 9 mice in each group, which were given vehicle PBS control and plasminogen, respectively. One day before modeling, mice were weighed and grouped. Then the model of cervical erosion was established. The cervix of the mouse was injected with 0.01 mL of phenol paste per day for 4 continuous treatments. Formulation scheme of phenolic paste: phenol was melted at 60° C., then 4 g Arabic gum powder and 5 mL distilled water were added to 3 mL of the phenol to stir and mix to obtain a milky viscous phenol paste[27]. After the model was established, plasminogen was administered to the plasminogen group at a dose of 1 mg/0.1 mL/mouse/day via tail vein injection, and the vehicle PBS control group was given the same volume of PBS. The day after modeling was day 0. On day 1, plasminogen or vehicle PBS was administered, and the administration period was 12 days. On day 5, day 9 and day 13, 3mice in both groups were randomly chosen, and the mice were sacrificed by taking blood from the eyeball, and the cervical tissue was fixed in 4% paraformaldehyde for 24-48 hours. After fixation, the cervical tissue was dehydrated with alcohol gradient and permeabilized by xylene and then embedded in paraffin. The thickness of the tissue section was 5 μm. The sections were dewaxed and rehydrated, and washed once, then repaired by citric acid for 30 minutes and cooled at room temperature for 10 minutes followed by gently rinse with water. Then the section was incubated with 3% hydrogen peroxide for 15 minutes and the tissue was circled by a PAP pen. The tissue was blocked in 10% normal goat serum (Vector laboratories, Inc., USA) for 1 hour; then the goat serum was discarded. Then it was incubated overnight at 4° C. in rabbit anti-mouse fibrin (fibrinogen) antibody (Abcam) and washed twice in TBS for 5 minutes each. Then it was incubated for 1 hour at room temperature with goat anti-rabbit IgG (HRP) (Abcam) secondary antibody and washed twice in TBS for 5 minutes each. The color was developed with a DAB kit (Vector laboratories, Inc., USA). After washing with water for 3 times, it was hematoxylin counterstained for 30 seconds and washed with running water for 5 minutes. The slices were gradiently dehydrated and permeabilized and observed under a microscope at 200 times.

Fibrinogen is a precursor of fibrin. In the presence of tissue damage, fibrinogen is hydrolyzed into fibrin as a stress response to the damage[28-30]. Therefore, fibrin levels can be used as a sign of the degree of damage.

Figure 4:
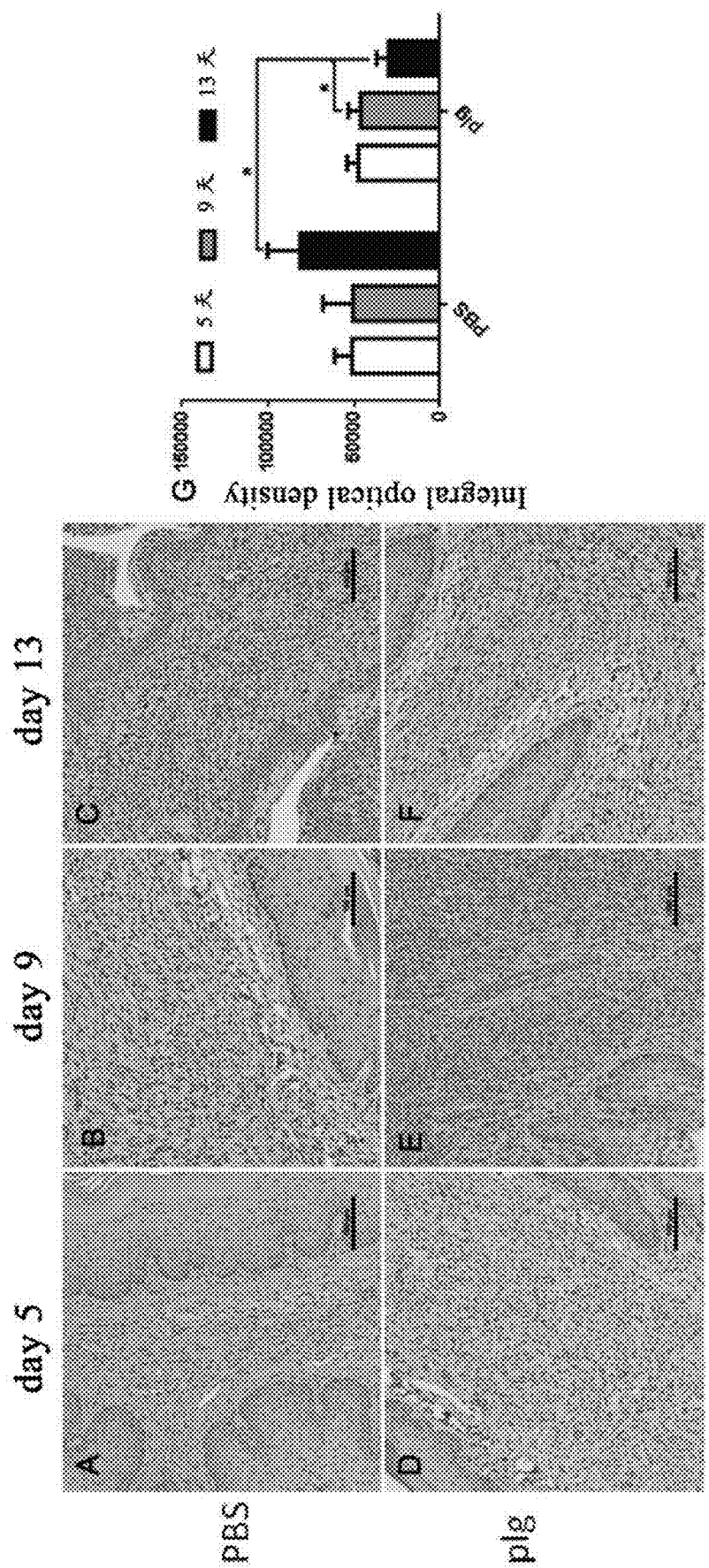
FIG. 4 shows the results by observing cervical fibrin immunostaining on day 5, day 9 and day 13 after the administration of plasminogen or PBS to plg−/− cervical erosion mouse model.

The results showed that the positive staining of fibrin was gradually deepened in the vehicle PBS control group (FIG. 4A-C). The positive staining in the plasminogen group (FIG. 4D-F) gradually became lighter, and there was a significant difference between the day 13 and the day 5 and 9, and compared with the vehicle PBS control group, the staining was lighter and there was a statistical difference at day 13 (FIG. 4G). plg-/- mice lack plasminogen, therefore, plasminogen was still lacking in mice given PBS vehicle, but plasminogen was replenished to mice in the plasminogen group. This means that plasminogen significantly reduced the deposition of fibrin, showing that plasminogen can promote repair of cervical injury in plg-/- cervical erosion mouse model.

Example 5 Plasminogen Promotes Inflammatory Repair in plg+/+ Cervical Erosion Mouse Model In this experiment, 12 healthy female plg+/+ mice aged 6-7 weeks were randomly divided into two groups,6 mice in each group, which were given vehicle PBS control and plasminogen, respectively. One day before modeling, mice were weighed and grouped. Then the model of cervical erosion was established. The cervix of the mouse was injected with 0.01 mL of phenol paste per day for 4 continuous treatments. Formulation scheme of phenolic paste: phenol was melted at 60° C., then 4 g Arabic gum powder and 5 mL distilled water were added to 3 mL of the phenol to stir and mix to obtain a milky viscous phenol paste[27]. After the model was established, plasminogen was administered to the plasminogen group at a dose of 1 mg/0.1 mL/mouse/day via tail vein injection, and the vehicle PBS control group was given the same volume of PBS. The day after modeling was day 0. On day 1, plasminogen or vehicle PBS was administered, and the administration period was 8 days. On day 5, day 9, 3mice in both groups were randomly chosen, and the mice were sacrificed by taking blood from the eyeball, and the cervical tissue was fixed in 4% paraformaldehyde for 24-48 hours. After fixation, the cervical tissue was dehydrated with alcohol gradient and permeabilized by xylene and then embedded in paraffin. The thickness of the tissue section was 5 μm. The sections were dewaxed and rehydrated, and washed once, then incubated in 3% hydrogen peroxide for 15 minutes, followed by 2 washes with water for 5 minutes each. Then the tissue was blocked in 10% normal goat serum (Vector laboratories, Inc., USA) for 1 hour; then the serum was threw off, and the tissue was circled by a PAP pen. Then it was incubated overnight at 4° C. in F4/80 Rabbit Polyclonal Antibody (Abcam) and washed twice in TBS for 5 minutes each. Then it was incubated for 1 hour at room temperature with goat anti-rabbit IgG (HRP) (Abcam) secondary antibody and washed twice in TBS for 5 minutes each. The color was developed with a DAB kit (Vector laboratories, Inc., USA). After washing with water for 3 times, it was hematoxylin counterstained for 30 seconds and washed with running water for 5 minutes. The slices were gradiently dehydrated and permeabilized and observed under a microscope at 400 times.

Figure 5:
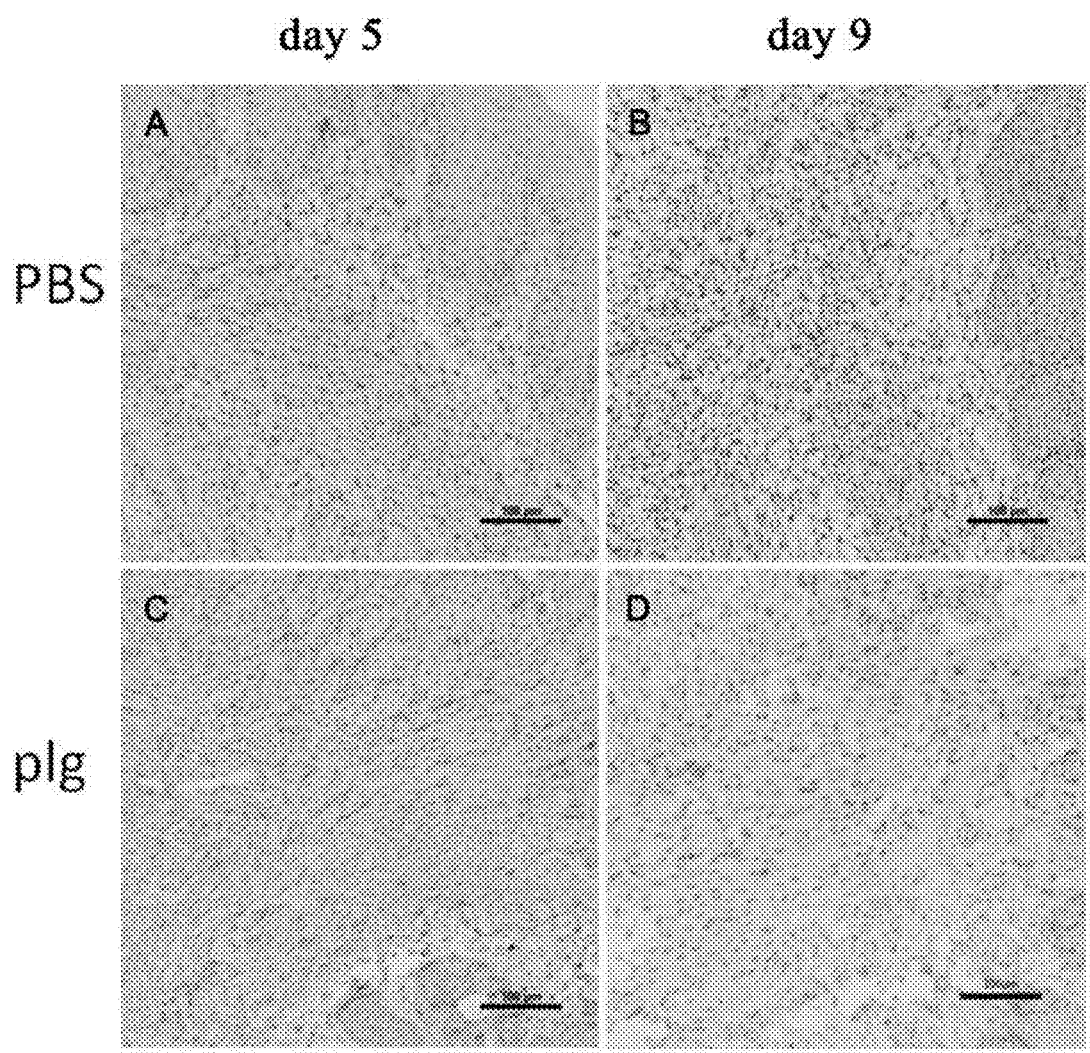
FIG. 5 shows the results of F4/80 immunostaining of the cervix on day 5 and day 9 after the administration of plasminogen or PBS to plg+/+ cervical erosion mouse model.

F4/80 is a macrophage marker that can indicate the degree and stage of an inflammatory response. The results showed that the positive expression levels of F4/80 in the cervix of the vehicle PBS control group (FIG. 5A, B) and the plasminogen group (FIG. 5C, D) were higher on day 9 than that on the day 5. However, the plasminogen group was significantly less than the vehicle PBS control group. This means that plasminogen can reduce the inflammation of the injured tissue, indicating that plasminogen can promote the repair of cervical inflammation in injured plg+/+ cervical erosion mouse model.

Example 6 Plasminogen Promotes Inflammatory Repair in plg-/- Cervical Erosion Mouse Model In this experiment, 18 healthy female plg$^{-/-}$ mice aged 6-7 weeks were randomly divided into two groups, 9 mice in each group, which were given vehicle PBS control and plasminogen, respectively. One day before modeling, mice were weighed and grouped. Then the model of cervical erosion was established. The cervix of the mouse was injected with 0.01 mL of phenol paste per day for 4 continuous treatments. Formulation scheme of phenolic paste: phenol was melted at 60° C., then 4 g Arabic gum powder and 5 mL distilled water were added to 3 mL of the phenol to stir and mix to obtain a milky viscous phenol paste[27]. After the model was established, plasminogen was administered to the plasminogen group at a dose of 1 mg/0.1 mL/mouse/day via tail vein injection, and the vehicle PBS control group was given the same volume of PBS. The day after modeling was day 0. On day 1, plasminogen or vehicle PBS was administered, and the administration period was 8 days. On day 5, day 9 and day 13, 3mice in both groups were randomly chosen, and the mice were sacrificed by taking blood from the eyeball, and the cervical tissue was fixed in 4% paraformaldehyde for 24-48 hours. After fixation, the cervical tissue was dehydrated with alcohol gradient and permeabilizedby xylene and then embedded in paraffin. The thickness of the tissue section was 5 μm. The sections were dewaxed and rehydrated, and washed once, then incubated in 3% hydrogen peroxide for 15 minutes, followed by 2 washes with water for 5 minutes each. Then the tissue was blocked in 10% normal goat serum (Vector laboratories, Inc., USA) for 1 hour; then the serum was threw off, and the tissue was circled by a PAP pen. Then it was incubated overnight at 4° C. in F4/80 Rabbit Polyclonal Antibody (Abcam) and washed twice in TBS for 5 minutes each. Then it was incubated for 1 hour at room temperature with goat anti-rabbit IgG (HRP) (Abcam) secondary antibody and washed twice in TBS for 5 minutes each. The color was developed with a DAB kit (Vector laboratories, Inc., USA). After washing with water for 3 times, it was hematoxylin counterstained for 30 seconds and washed with running water for 5 minutes. The slices were gradiently dehydrated and permeabilized and observed under a microscope at 400 times.

Figure 6:
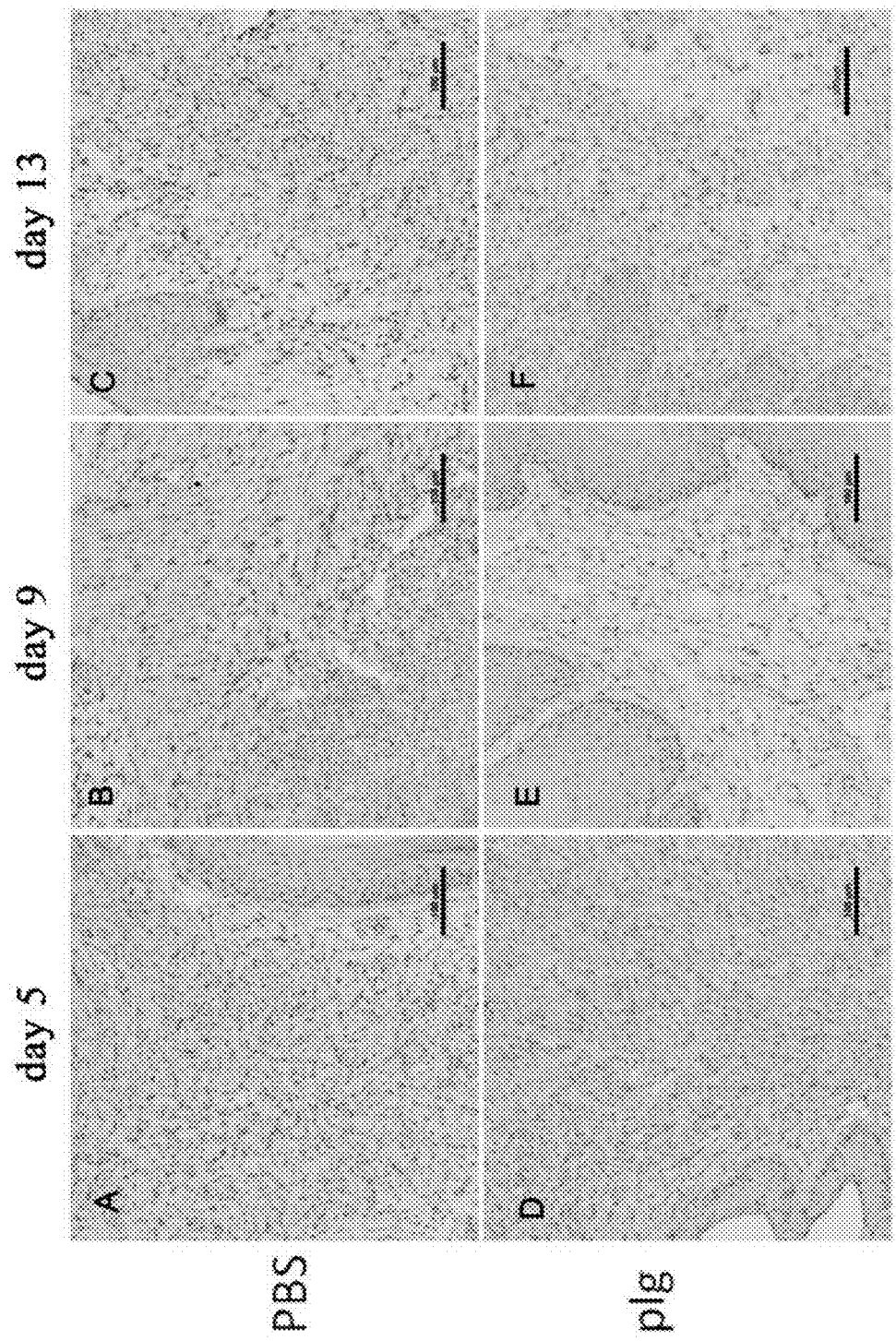
FIG. 6 shows the results of F4/80 immunostaining of the cervix on day 5, day 9 and day 13 after the administration of plasminogen or PBS to plg−/− cervical erosion mouse model.

F4/80 is a macrophage marker that can indicate the degree and stage of an inflammatory response. The results showed that there was no significant change in positive expression levels of F4/80 on day 5, 9 and 13 for the vehicle PBS control group (FIG. 6A-C) and the plasminogen group (FIG. 6D-F). However, the positive expression of plasminogen group was lower than that of vehicle PBS control group. plg-/- mice lack plasminogen, therefore, plasminogen was still lacking in mice given PBS vehicle, but plasminogen was replenished to mice in the plasminogen group. This means that plasminogen can reduce the level of inflammation in the injured tissue, indicating that plasminogen can promote inflammatory repair of the cervix in plg-/- cervical erosion mouse model.

REFERENCES

[1] Tang Wen-en. Relationship between cervical reserve cells and erosion and carcinogenesis. Journal of Beijing Medical University. 1993, 25 (1): 61.
[2] Le Jie. Obstetrics and Gynecology [M]. Fifth Edition. Beijing: People's Medical Publishing House, 2000, 291.
[3] Zhi Hua. Modern Venereal Medicine [M]. First Edition. Guangzhou: Guangdong People's Publishing House. 1996: 288-289.
[4] Lu Chun, Zhu Guoxing, Huang Huaiqiu. Clinical analysis of ureaplasma urealyticum on cervical pathogenicity [J]. Journal of Clinical Dermatology, 2002; 31: 150.
[5] Wu Nanping, Wang Xinzi, Wu Lingjiao, et al. Preliminary study of detection of mycoplasma in 65 patients with cervix herpesvirus[J]. The Chinese Journal of Dermatovenereology,1997; 11:385.
[6] Alexander C M and Werb, Z. (1991). Extracellular matrix degradation. In Cell Biology of Extracellular Matrix, Hay E D, ed. (New York: Plenum Press), pp. 255-302
[7] Werb, Z., Mainardi, C. L., Vater, C. A., and Harris, E. D., Jr. (1977). Endogenous activiation of latent collagenase by rheumatoid synovial cells. Evidence for a role of plasminogen activator. N. Engl. J. Med. 296, 1017-1023.
[8] He, C. S., Wilhelm, S. M., Pentland, A. P., Marmer, B. L., Grant, G. A., Eisen, A. Z., and Goldberg, G. I. (1989). Tissue cooperation in a proteolytic cascade activating human interstitial collagenase. Proc. Natl. Acad. Sci. U.S.A 86, 2632-2636
[9] Stoppelli, M. P., Corti, A., Soffientini, A., Cassani, G., Blasi, F., and Assoian, R. K. (1985). Differentiation-enhanced binding of the amino-terminal fragment of human urokinase plasminogen activator to a specific receptor on U937 monocytes. Proc. Natl. Acad. Sci. U.S.A 82, 4939-4943.
[10] Vassalli, J. D., Baccino, D., and Belin, D. (1985). A cellular binding site for the Mr 55, 000 form of the human plasminogen activator, urokinase. J. Cell Biol. 100, 86-92.
[11] Wiman, B. and Wallen, P. (1975). Structural relationship between "glutamic acid" and "lysine" forms of human plasminogen and their interaction with the NH2-terminal activation peptide as studied by affinity chromatography. Eur. J. Biochem. 50, 489-494.
[12] Saksela, O. and Rifkin, D. B. (1988). Cell-associated plasminogen activation: regulation and physiological functions. Annu. Rev. Cell Biol. 4, 93-126
[13] Raum, D., Marcus, D., Alper, C. A., Levey, R., Taylor, P. D., and Starzl, T. E. (1980). Synthesis of human plasminogen by the liver. Science 208, 1036-1037
[14] Wallén P (1980). Biochemistry of plasminogen. In Fibrinolysis, Kline D L and Reddy K K N, eds. (Florida: CRC
[15] Sottrup-Jensen, L., Zajdel, M., Claeys, H., Petersen, T. E., and Magnusson, S. (1975). Amino-acid sequence of activation cleavage site in plasminogen: homology with "pro" part of prothrombin. Proc. Natl. Acad. Sci. U.S.A 72, 2577-2581.
[16] Collen, D. and Lijnen, H. R. (1991). Basic and clinical aspects of fibrinolysis and thrombolysis. Blood 78, 3114-3124.
[17] Alexander, C. M. and Werb, Z. (1989). Proteinases and extracellular matrix remodeling. Curr. Opin. Cell Biol. 1, 974-982.
[18] Mignatti, P. and Rifkin, D. B. (1993). Biology and biochemistry of proteinases in tumor invasion. Physiol Rev. 73, 161-195.
[19] Collen, D. (2001). Ham-Wasserman lecture: role of the plasminogen system in fibrin-homeostasis and tissue remodeling. Hematology. (Am. Soc. Hematol. Educ. Program. ) 1-9.
[20] Rifkin, D. B., Moscatelli, D., Bizik, J., Quarto, N., Blei, F., Dennis, P., Flaumenhaft, R., and Mignatti, P. (1990). Growth factor control of extracellular proteolysis. Cell Differ. Dev. 32, 313-318.

[21] Andreasen, P. A., Kjoller, L., Christensen, L., and Duffy, M. J. (1997). The urokinase-type plasminogen activator system in cancer metastasis: a review. Int. J. Cancer 72, 1-22.
[22] Rifkin, D. B., Mazzieri, R., Munger, J. S., Noguera, I., and Sung, J. (1999). Proteolytic control of growth factor availability. APMIS 107, 80-85.
[23] Marder V J, Novokhatny V. Direct fibrinolytic agents: biochemical attributes, preclinical foundation and clinical potential [J]. Journal of Thrombosis and Haemostasis, 2010, 8(3): 433-444.
[24] Hunt J A, Petteway Jr S R, Scuderi P, et al. Simplified recombinant plasmin: production and functional comparison of a novel thrombolytic molecule with plasma-derived plasmin[J]. Thromb Haemost, 2008, 100(3): 413-419.
[25] Sottrup-Jensen L, Claeys H, Zajdel M, et al. The primary structure of human plasminogen: Isolation of two lysine-binding fragments and one "mini"-plasminogen (MW, 38, 000) by elastase-catalyzed-specific limited proteolysis [J]. Progress in chemical fibrinolysis and thrombolysis, 1978, 3: 191-209.
[26] Nagai N, Demarsin E, Van Hoef B, et al. Recombinant human microplasmin: production and potential therapeutic properties[J]. Journal of Thrombosis and Haemostasis, 2003, 1(2): 307-313.
[27] Kong Lingxuan, Song Yanping, and Wang Qing. Therapeutic effects of compound sea buckthorn seed oil suppositories on animal models of vaginal and cervical erosion in rats. Journal of Medicine of Shaanxi College of Traditional Chinese Medicine. 2008 Vol. 9 No. 1[28]Jae Kyu Ryu, Mark A. Petersen, Sara G. Murray et al. Blood coagulation protein fibrinogen promotes autoimmunity and demyelination via chemokine release and antigen presentation. NATURE COMMUNICATIONS,2015, 6:8164.
[29] Dimitrios Davalos , Katerina Akassoglou. Fibrinogen as a key regulator of inflammation in disease. Seminars in Immunopathology, 2012, 34(1):43-62.
[30] Valvi D, Mannino D M, Mullerova H, et al. Fibrinogen, chronic obstructive pulmonary disease (COPD) and outcomes in two United States cohorts. Int J Chron Obstruct Pulmon Dis 2012; 7:173-82.

The invention claimed is:

1. A method of treating cervical erosion in a subject in need thereof, comprising administering to the subject an effective amount of plasminogen.

2. The method according to claim 1, wherein the cervical erosion comprises true erosion or pseudo-erosion.

3. The method according to claim 1, wherein the plasminogen has at least 80%, 85%, 90%, 95%, 96%, 97%, 98% or 99% sequence identity with SEQ ID NO. 2, 6, 8, 10 or 12 and still has plasminogen activity.

4. The method according to claim 1, wherein the plasminogen is a protein comprising a plasminogen active fragment and still having plasminogen activity.

5. The method according to claim 1, wherein the plasminogen is selected from variants of Glu-plasminogen, Lys-plasminogen, mini-plasminogen, micro-plasminogen, δ-plasminogen or any combination thereof.

6. The method according to claim 1, wherein in one embodiment, the plasminogen is a conservative substitution variants elected from variants of Glu-plasminogen, Lys-plasminogen, mini-plasminogen, δ(delta)-plasminogen or micro-plasminogen.

7. The method according to claim 1, wherein the plasminogen is human native plasminogen as shown in SEQ ID NO. 2.

8. The method according to claim 1, wherein the plasminogen is administered systemically or topically.

9. The method according to claim 1, wherein the plasminogen is administered in combination with other drugs or therapies.

10. The method according to claim 9, wherein the other drugs or therapies comprise anti-bacterial drugs, anti-viral drugs, anti-fungal drugs, anti-thrombotic drugs, anti-diabetic drugs, physiotherapy, laser therapy, and local surgery therapy.

11. The method according to claim 1, wherein the plasminogen is administered by intravenous, intramuscular, subcutaneous, local injection, rectal, or vaginal administration.

* * * * *